US012268598B2

(12) United States Patent
Cohen-Tzemach et al.

(10) Patent No.: US 12,268,598 B2
(45) Date of Patent: Apr. 8, 2025

(54) MECHANICALLY EXPANDABLE PROSTHETIC HEART VALVE AND DELIVERY APPARATUS

(71) Applicant: Edwards Lifesciences Corporation, Irvine, CA (US)

(72) Inventors: Hanoch Cohen-Tzemach, Holon (IL); Tamir S. Levi, Zikhron Yaakov (IL); Yair A. Neumann, Moshav Sede Varburg (IL); Tomer Saar, Pardes Hanna-Karkur (IL); Gregory Rinberg, Haifa (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 743 days.

(21) Appl. No.: 17/337,711

(22) Filed: Jun. 3, 2021

(65) Prior Publication Data
US 2021/0282922 A1  Sep. 16, 2021

Related U.S. Application Data

(63) Continuation of application No. PCT/US2019/064373, filed on Dec. 4, 2019.
(Continued)

(51) Int. Cl.
*A61F 2/24* (2006.01)

(52) U.S. Cl.
CPC ............ *A61F 2/243* (2013.01); *A61F 2/2418* (2013.01); *A61F 2/2439* (2013.01); *A61F 2230/0091* (2013.01)

(58) Field of Classification Search
CPC ...... A61F 2/243; A61F 2/2418; A61F 2/2439; A61F 2230/0091; A61F 2220/0041; A61F 2220/0091; A61F 2250/001
See application file for complete search history.

(56) References Cited

U.S. PATENT DOCUMENTS 3,409,013 A   11/1968  Berry
3,548,417 A   12/1970  Kisher
(Continued)

FOREIGN PATENT DOCUMENTS

CN   107645941 A   1/2018
DE     0144167 C   9/1903
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Leslie A Lopez
*Assistant Examiner* — Kia Xiong White
(74) *Attorney, Agent, or Firm* — Klarquist Sparkman, LLP; Joel B. German

(57) ABSTRACT

A radially expandable prosthetic valve can comprise an annular frame, at least one expansion mechanism and a cord. The annular frame can be radially collapsible and expandable between a radially collapsed configuration and a radially expanded configuration. The expansion mechanism can comprise a first member attached to the frame at a first location and a second member attached to the frame at a second location axially spaced from the first location. The cord can extend at least partially along the expansion mechanism in a first direction, be reeved around a portion of the second member, and extend at least partially along the expansion mechanism in a second direction opposite the first direction. Applying a proximally directed force to a first portion of the cord can cause the second member to move relative to the first member, which can cause the frame to foreshorten axially and expand radially.

26 Claims, 12 Drawing Sheets

Related U.S. Application Data

(60) Provisional application No. 62/776,348, filed on Dec. 6, 2018.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |

(56) References Cited

U.S. PATENT DOCUMENTS

| | | |
|---|---|---|
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Fidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112355 A1 | 5/2007 | Salahieh et al. |
| 2007/0112422 A1 | 5/2007 | Dehdashtian |
| 2007/0162102 A1 | 7/2007 | Ryan et al. |
| 2007/0203503 A1* | 8/2007 | Salahieh .............. A61F 2/2436 623/2.11 |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1* | 10/2014 | Cartledge ............. A61F 2/2412 623/1.11 |
| 2014/0330368 A1* | 11/2014 | Gloss .................... A61F 2/243 623/2.11 |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0256271 A1* | 9/2016 | Backus ................. A61F 2/2418 |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |

(56) References Cited

U.S. PATENT DOCUMENTS

| | | | |
|---|---|---|---|
| 2019/0192288 A1 | 6/2019 | Levi et al. | |
| 2019/0192289 A1 | 6/2019 | Levi et al. | |

FOREIGN PATENT DOCUMENTS

| | | | |
|---|---|---|---|
| DE | 2246526 | A1 | 3/1973 |
| DE | 19532846 | A1 | 3/1997 |
| DE | 19546692 | A1 | 6/1997 |
| DE | 19857887 | A1 | 7/2000 |
| DE | 19907646 | A1 | 8/2000 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| EP | 0103546 | A1 | 3/1984 |
| EP | 0850607 | A1 | 7/1998 |
| EP | 1057460 | A1 | 12/2000 |
| EP | 1088529 | A2 | 4/2001 |
| EP | 1570809 | A1 | 9/2005 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 9117720 | A1 | 11/1991 |
| WO | 9217118 | A1 | 10/1992 |
| WO | 9301768 | A1 | 2/1993 |
| WO | 9724080 | A1 | 7/1997 |
| WO | 9829057 | A1 | 7/1998 |
| WO | 9930646 | A1 | 6/1999 |
| WO | 9933414 | A1 | 7/1999 |
| WO | 9940964 | A1 | 8/1999 |
| WO | 9947075 | A1 | 9/1999 |
| WO | 0018333 | A1 | 4/2000 |
| WO | 0041652 | A1 | 7/2000 |
| WO | 0135878 | A2 | 5/2001 |
| WO | 0149213 | A2 | 7/2001 |
| WO | 0154624 | A1 | 8/2001 |
| WO | 0154625 | A1 | 8/2001 |
| WO | 0162189 | A1 | 8/2001 |
| WO | 0047139 | A9 | 9/2001 |
| WO | 0164137 | A1 | 9/2001 |
| WO | 0176510 | A2 | 10/2001 |
| WO | 0222054 | | 3/2002 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 0249540 | A2 | 6/2002 |
| WO | 03047468 | | 6/2003 |
| WO | 2005034812 | A1 | 4/2005 |
| WO | 2005055883 | A1 | 6/2005 |
| WO | 2005084595 | A1 | 9/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2005102015 | A3 | 4/2007 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010121076 | A2 | 10/2010 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

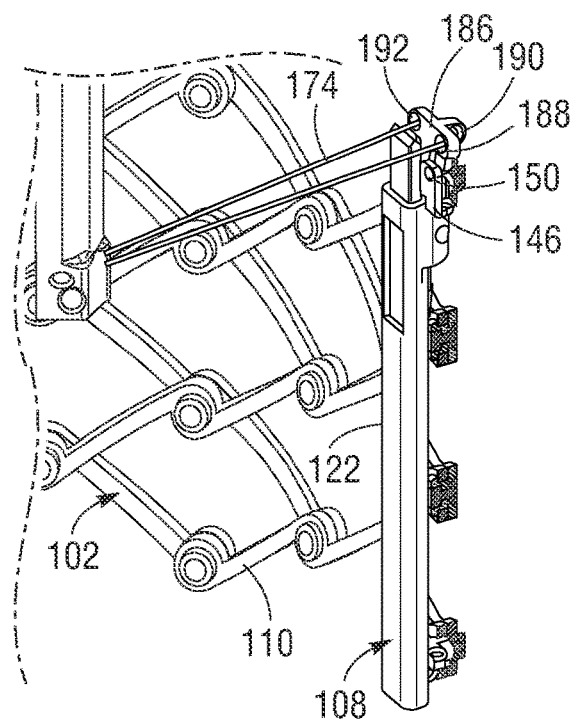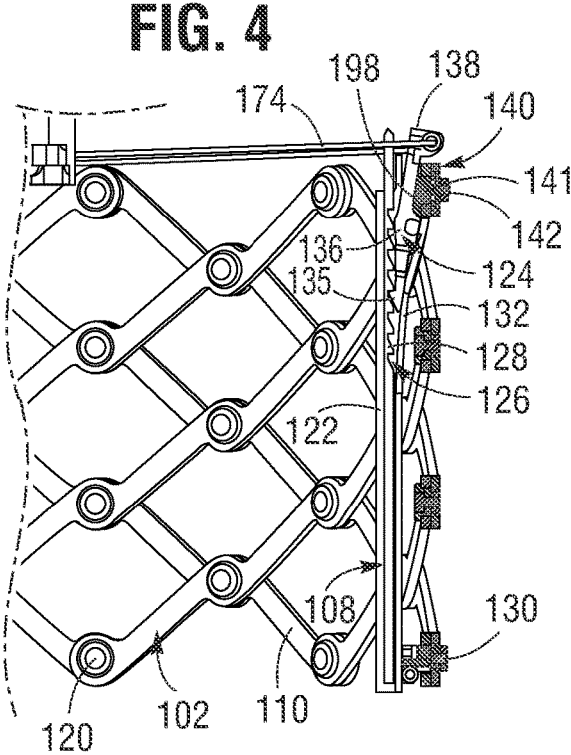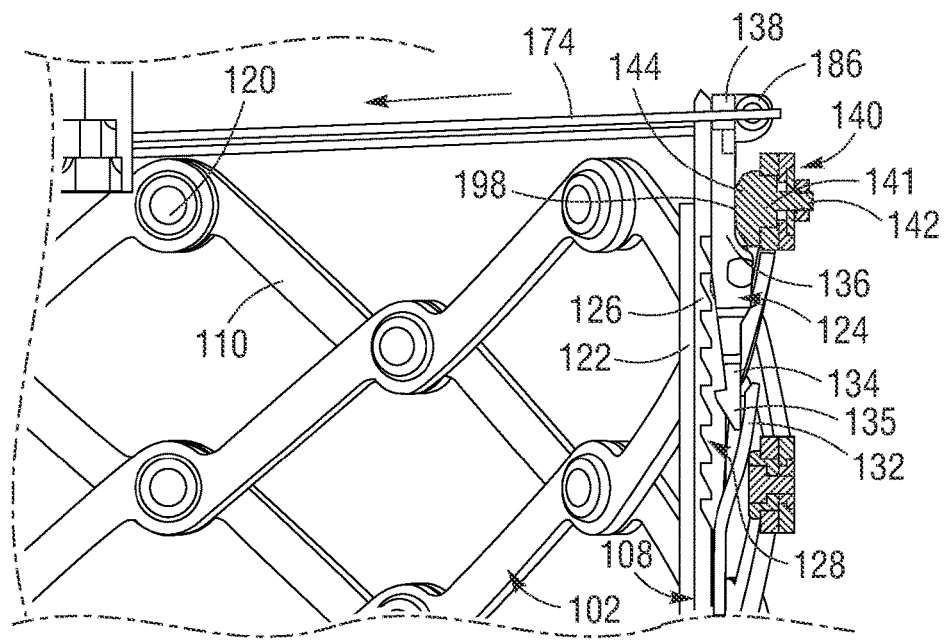

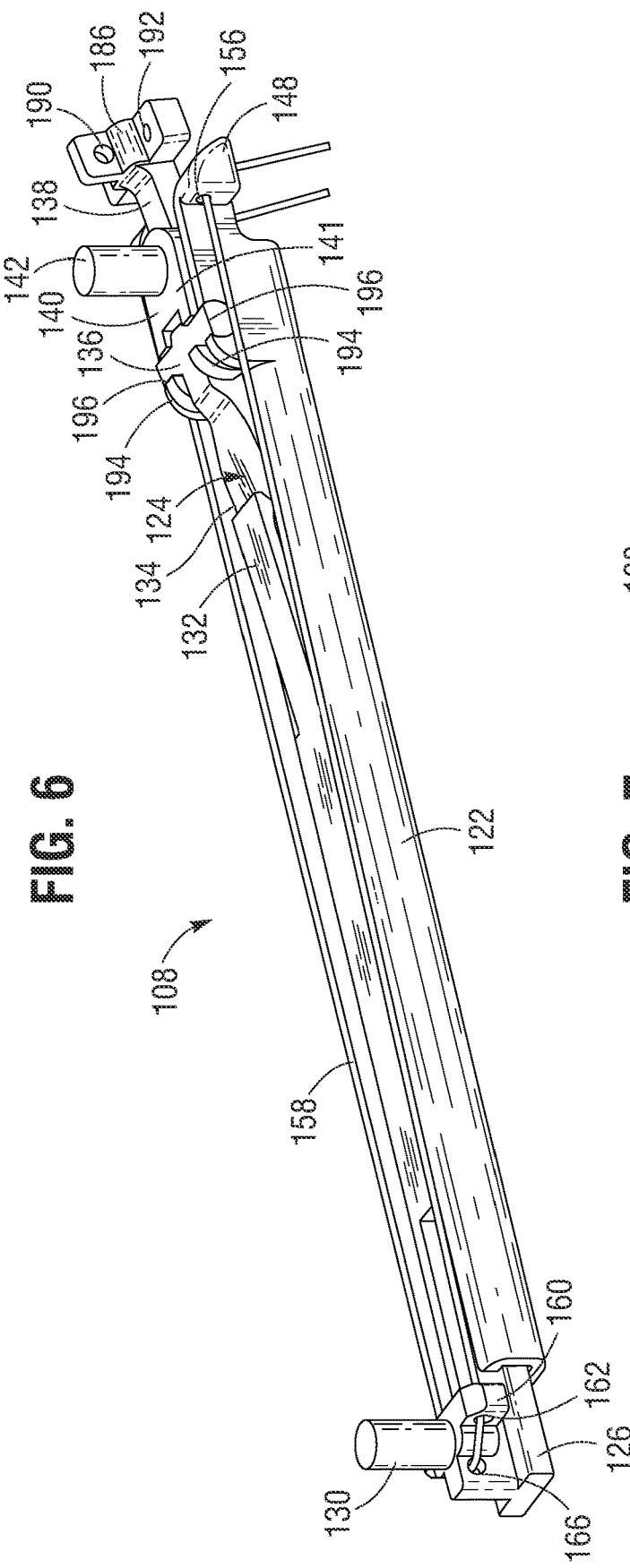
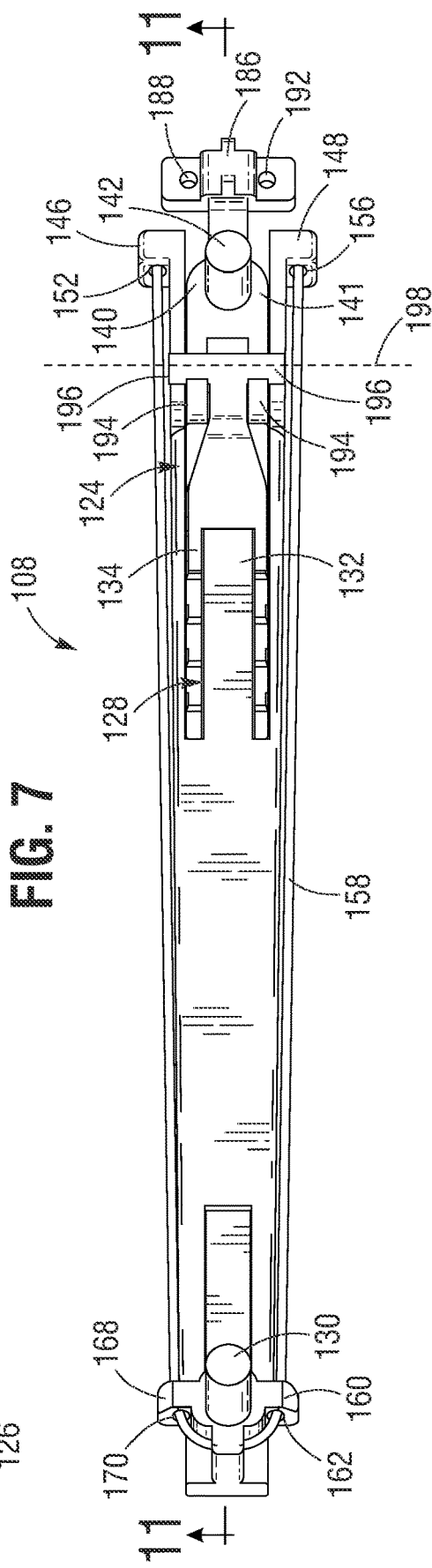

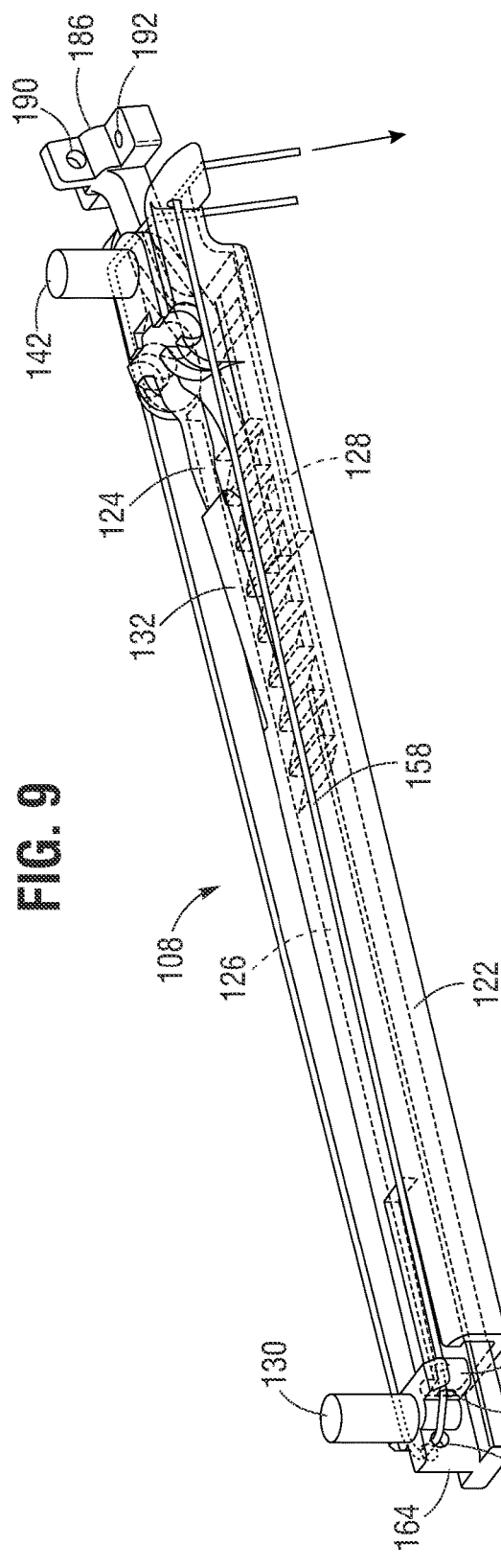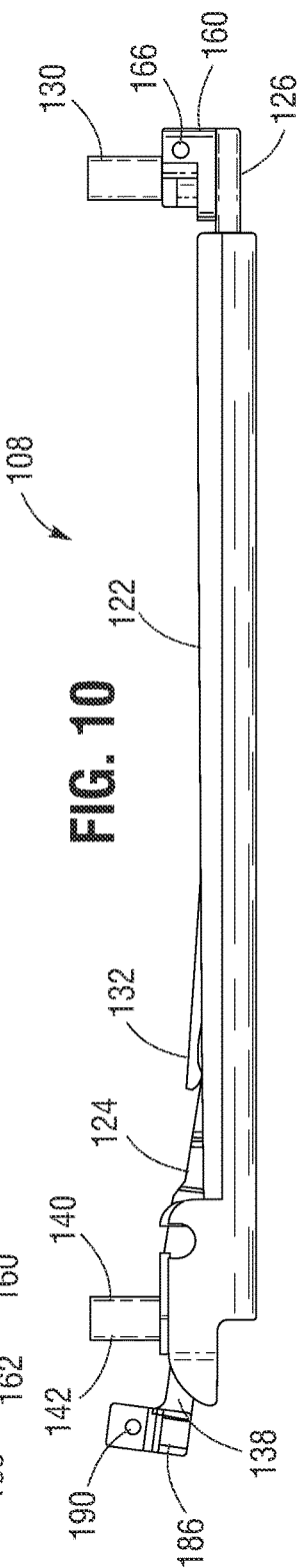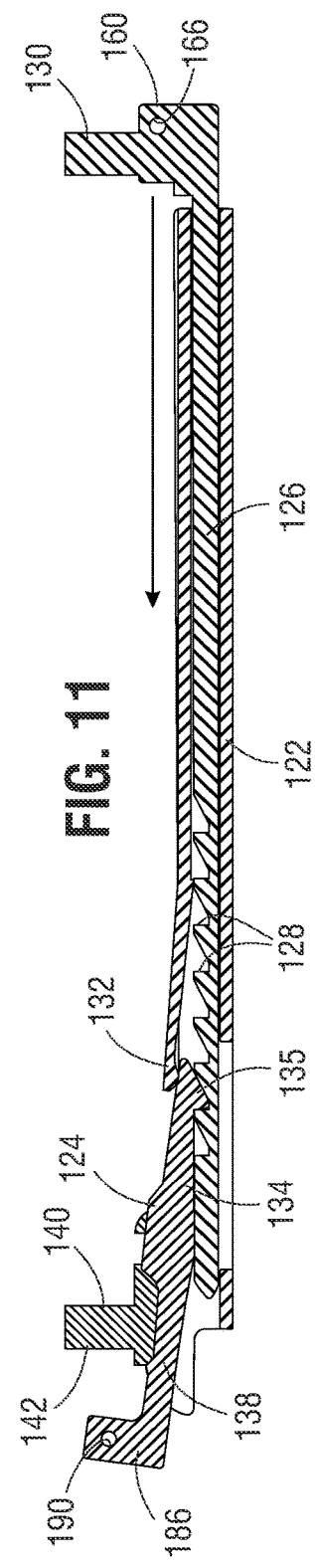

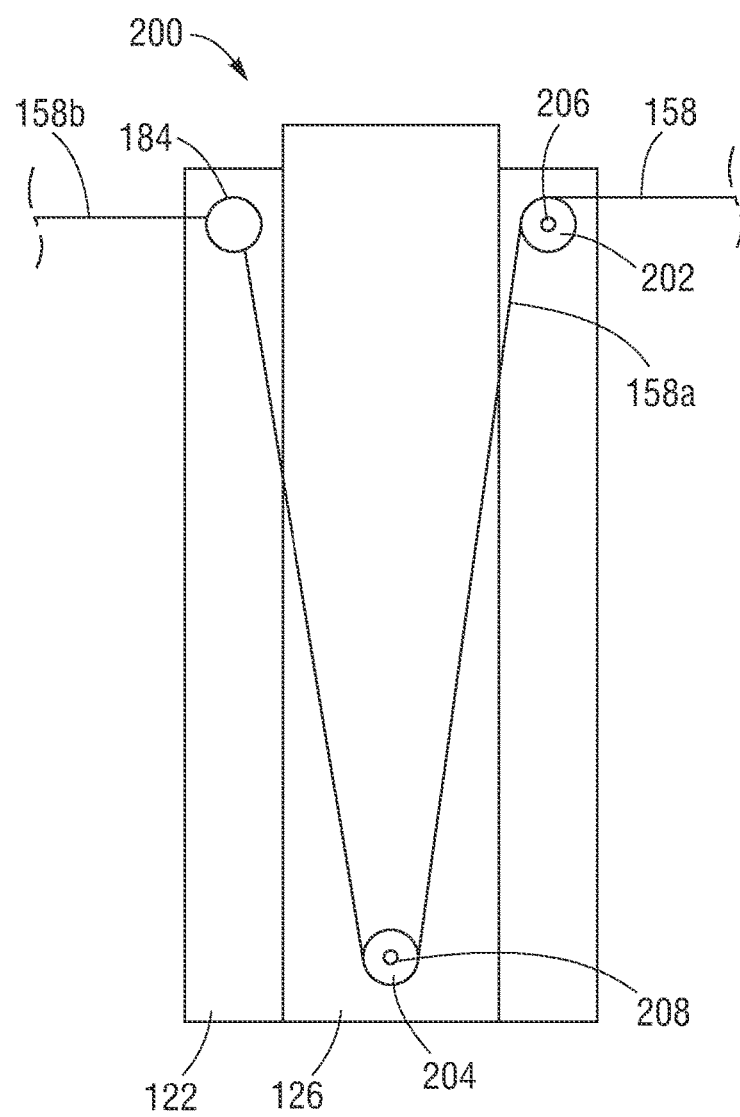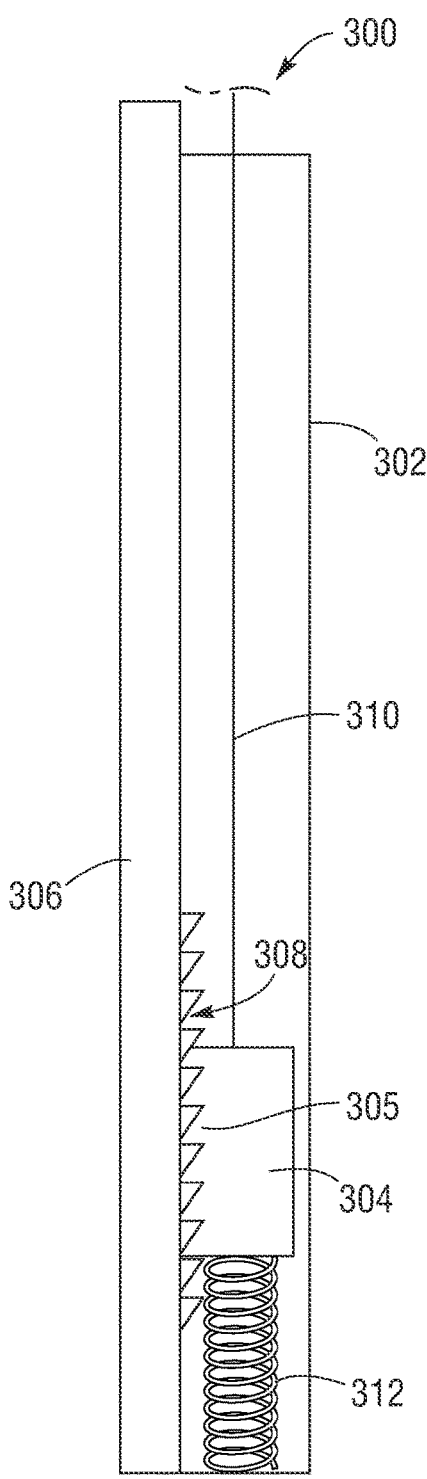

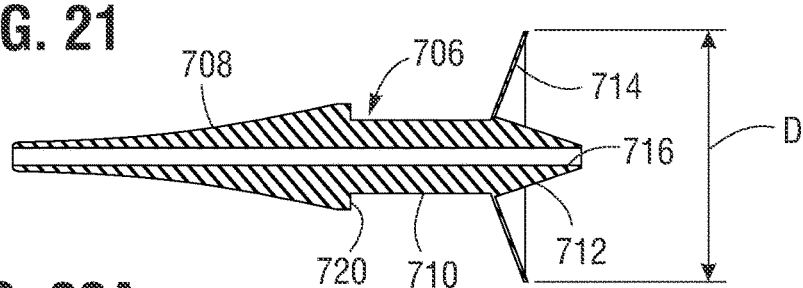
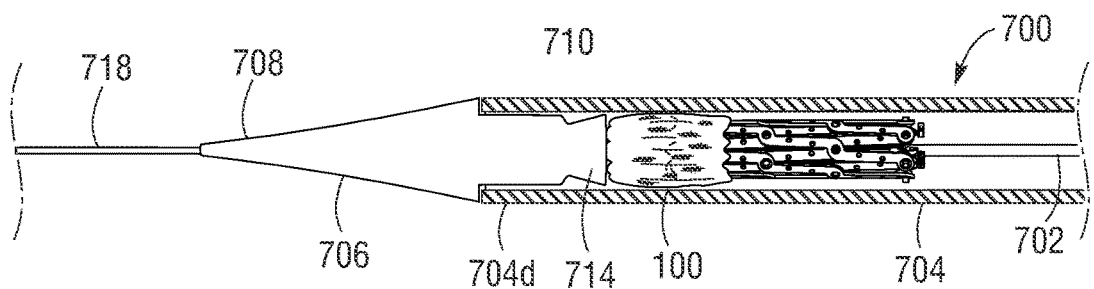
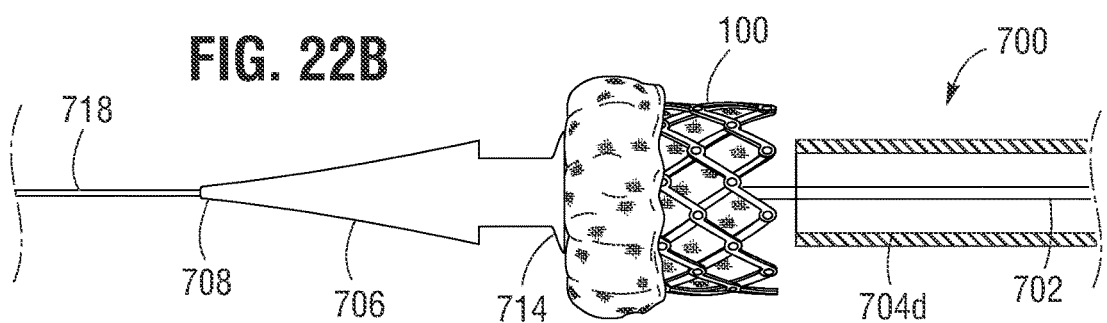
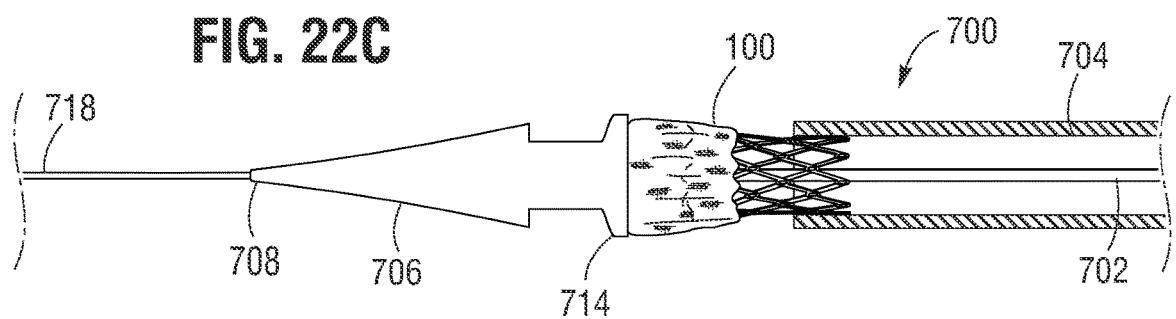
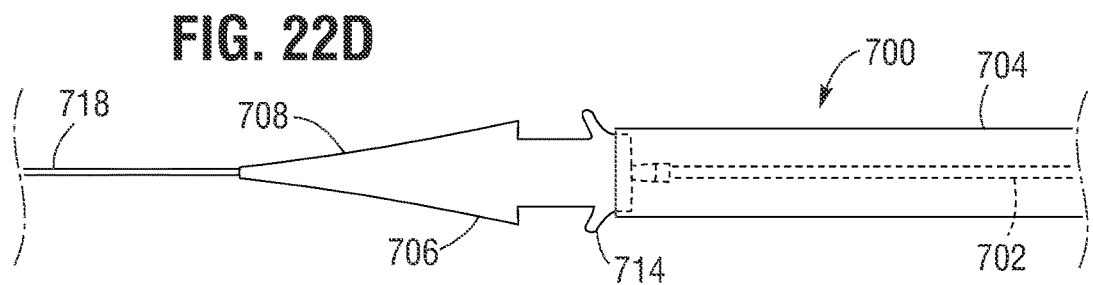

MECHANICALLY EXPANDABLE PROSTHETIC HEART VALVE AND DELIVERY APPARATUS

CROSS-REFERENCE TO RELATED APPLICATIONS

The present application is a continuation of PCT Application No. PCT/US2019/064373, filed Dec. 4, 2019, which claims the benefit of U.S. Provisional Application No. 62/776,348, filed on Dec. 6, 2018, both of which applications are incorporated herein by reference.

FIELD

The present disclosure relates to implantable, mechanically expandable prosthetic devices, such as prosthetic heart valves, and to methods and delivery assemblies for, and including, such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Because of the drawbacks associated with conventional open-heart surgery, percutaneous and minimally-invasive surgical approaches are garnering attention. In one technique, a prosthetic device is configured to be implanted in a less invasive procedure by way of catheterization. For example, a collapsible transcatheter prosthetic heart valve can be crimped to a compressed state and percutaneously introduced in the compressed state on a catheter and expanded to a functional size at the desired position by mechanical expansion or using a self-expanding frame or stent. Despite the recent advancements in percutaneous valve technology, there remains a need for improved transcatheter heart valves and delivery devices for such valves.

SUMMARY

Embodiments of a mechanically expandable prosthetic heart valve and delivery apparatus are disclosed herein. In one representative embodiment, a radially expandable prosthetic valve can comprise an annular frame, at least one expansion mechanism and a cord. The annular frame can comprise an inflow end and an outflow end and can be radially collapsible and expandable between a radially collapsed configuration and a radially expanded configuration. The expansion mechanism can comprise a first member attached to the frame at a first location and a second member attached to the frame at a second location axially spaced from the first location. The cord can extend at least partially along the expansion mechanism in a first direction, can reeved around a portion of the second member, and can extend at least partially along the expansion mechanism in a second direction opposite the first direction. Applying a proximally directed force to a first portion of the cord can cause the cord to move relative to the second member and the second member to move relative to the first member, which can cause the frame to foreshorten axially and expand radially.

In some embodiments, the prosthetic valve can include a leaflet structure positioned within the frame and secured thereto.

In some embodiments, applying a proximally directed force to a second portion of the cord can release the cord from the expansion mechanism.

In some embodiments, the prosthetic valve can further comprise a stop member coupled to the cord and sized to prevent the cord from being pulled through the expansion mechanism when the proximally directed force is applied to the first portion of the cord. In some embodiments, the stop member can comprise a knot.

In some embodiments, the expansion mechanism can further comprise a housing and the second member can be slidable at least partially within the housing. In some embodiments, the cord can extend through a first portion of the housing, around the portion of the second member and through a second portion of the housing, in that order.

In some embodiments, applying the proximally directed force to the first portion of the cord can pull the second member through the housing towards the first location on the frame. In some embodiments, the prosthetic valve can further comprise a locking mechanism configured to retain the frame in the radially expanded configuration.

In some embodiments, the expansion mechanism can comprise a ratchet assembly. In some embodiments, the first member can comprise one of a rack and a pawl of the ratchet assembly and the second member can comprise the other of the rack and the pawl of the ratchet assembly.

In some embodiments, the rack can comprise an elongated bar comprising a plurality of ratchet teeth arrayed along a length of the bar, the rack can be movable with respect to the pawl, applying the proximally directed force to the first portion of the cord can cause the rack to move in the second direction thereby causing the annular frame to foreshorten axially and expand radially, and engagement of the pawl with one of the ratchet teeth can prevent movement of the rack in the first direction to prevent radial compression of the annular frame.

In some embodiments, the pawl can comprise an engagement portion, a release portion and an intermediate portion. The engagement portion can be configured to engage the ratchet teeth of the rack, the release portion can extend away from the rack, and the intermediate portion can be positioned between the engagement portion and the release portion. An inwardly directed radial force applied to the release portion can cause the engagement portion to disengage from the ratchet teeth to allow movement of the pawl along the rack in the first direction.

In some embodiments, the cord can be a first cord and the prosthetic valve can further comprise a second cord connected to the release portion of the pawl such that a pulling force applied to the second cord causes the engagement portion to disengage from the ratchet teeth. In some embodiments, the second cord can comprise a loop that extends through first and second openings in the release portion of the pawl.

In some embodiments, the at least one expansion mechanism can comprise at least two expansion mechanisms and the second cord of each expansion mechanism can be configured such that a pulling force applied to the second cord of each expansion mechanism causes the frame to compress radially.

In some embodiments, the frame can comprise a plurality of struts connected to each other at a plurality of pivot joints and the second member can comprise a post that extends into openings in two of the struts to form one of the pivot joints.

In some embodiments, the expansion mechanism can further comprise a retaining member configured to apply a biasing force to the pawl so as to resiliently retain the pawl in engagement with the rack.

In some embodiments, the portion of the second member around which the cord is reeved can be a pulley. In some embodiments, the cord can be a suture. In some embodiments, the second cord can be a suture. In some embodiments, the prosthetic valve cab be in combination with a delivery apparatus comprising a handle. The first portion of the cord can be operatively connected to the handle.

In some embodiments, the expansion mechanism can further comprise a biasing member configured to exert a biasing force against the second member in the second direction. The biasing force can be selected such that when the prosthetic valve is implanted within a native heart valve annulus, the second member is caused to move in the second direction under the biasing force and further expand the frame as the native annulus enlarges over time. In some embodiments, the biasing member can comprise a spring.

In another representative embodiment, a radially expandable prosthetic valve can comprise an annular frame, at least one expansion mechanism and a cord. The annular frame can comprise an inflow end and an outflow end and can be radially collapsible and expandable between a radially collapsed configuration and a radially expanded configuration. The expansion mechanism can comprise a first member attached to the frame at a first location and a second member attached to the frame at a second location axially spaced from the first location. The cord can be operatively connected to the first and second members such that applying a force to the cord causes the second member to move relative to the first member with a mechanical advantage greater than 1. Movement of the second member relative to the first member can cause the frame to radially expand.

In some embodiments, the prosthetic valve can further comprise a leaflet structure positioned within the frame and secured thereto. In some embodiments, the mechanical advantage can be at least 2:1. In some embodiments, the cord can extend distally at least partially along the expansion mechanism, around a portion of the second member, and proximally at least partially along the expansion mechanism.

In another representative embodiment, a radially expandable prosthetic valve can comprise an annular frame, at least one expansion member, and a biasing member. The annular frame can comprise an inflow end and an outflow end and can be radially collapsible and expandable between a radially compressed configuration and a radially expanded configuration. The expansion mechanism can comprise a first member attached to the frame at a first location and a second member attached to the frame at a second location axially spaced from the first location. Movement of the first member relative to the second member in a first direction can cause the frame to radially expand and movement of the first member relative to the second member in a second direction, opposite the first direction, can cause the frame to radially compress. The biasing member can be configured to exert a biasing force against the first member in the first direction. The biasing force can be selected such that when the prosthetic valve is implanted within a native heart valve annulus, the first member is caused to move relative to the second member under the biasing force in the first direction and further expand the frame as the native annulus enlarges over time.

In some embodiments, the expansion mechanism can comprise a ratchet assembly. In some embodiments, the first member can comprise one of a rack and a pawl of the ratchet assembly and the second member comprises the other of the rack and the pawl of the ratchet assembly. In some embodiments, the biasing member can comprise a spring.

In another representative embodiment, a radially expandable prosthetic valve can comprise an annular frame, at least one expansion mechanism, and a biasing member. The annular frame can comprise an inflow end and an outflow end and can be radially collapsible and expandable between a radially compressed configuration and a radially expanded configuration. The expansion mechanism can comprise a first member attached to the frame at a first location, a second member attached to the frame at a second location axially spaced from the first location, and a third member attached to the frame at a third location axially spaced from the first and second locations. Movement of the first member relative to the second member in a first direction can cause the frame to radially expand and movement of the first member relative to the second member in a second direction, opposite the first direction, can cause the frame to radially compress. The biasing member can be operatively connected to the first member and the third member such that a potential energy of the biasing member increases when the first member is moved relative to the second member to radially expand the frame from the radially compressed configuration to the radially expanded configuration. The potential energy of the biasing member can exert a biasing force against the third member that causes the third member to move relative to the second member and further expand the frame as a native annulus in which the prosthetic valve is implanted enlarges over time.

In some embodiments, the biasing member can comprise a spring. In some embodiments, the first member and the second member can collectively comprise a ratchet assembly. The first member can comprise one of a rack and a pawl of the ratchet assembly, and the second member can comprise the other of the rack and the pawl of the ratchet assembly. In some embodiments, the biasing member can be positioned between the first member and the third member such that the biasing member is compressed when the first member is moved relative to the second member to radially expand the frame.

In another representative embodiment, a medical assembly can comprise a radially expandable prosthetic valve and a delivery apparatus comprising a nose cone with a flared portion sized to cover a distal end portion of the prosthetic valve in a partially compressed configuration.

In another representative embodiment, a method of implanting a prosthetic heart valve can comprise inserting the prosthetic valve and a distal end portion of a delivery apparatus into a patient's vasculature, wherein the prosthetic heart valve is in a radially compressed state, positioning the prosthetic valve adjacent to a native valve of the patient's heart, and applying a proximally directed force to a first end of a first cord to cause the prosthetic valve to expand from the radially compressed state to a radially expanded state. The first cord can be operatively connected to the prosthetic valve such that the proximally directed force is transmitted to the prosthetic valve with a mechanical advantage greater than 1.

In some embodiments, the method can further comprise applying a proximally directed force to a second cord operatively connected to the prosthetic valve to cause the prosthetic valve to radially compress. In some embodiments, the method can further comprise applying a proximally directed force to a second end of the first cord to release the first cord from the prosthetic valve.

In another representative embodiment, a method of implanting a prosthetic heart valve can comprise inserting the prosthetic valve and a distal end portion of a delivery apparatus into a patient's vasculature, wherein the prosthetic valve is in a radially compressed state along the distal end portion of the delivery apparatus, and wherein the delivery apparatus comprises a nose cone, radially expanding the prosthetic valve from the radially compressed state to a radially expanded state, radially compressing the prosthetic valve to at least a partially compressed state, covering a distal end portion of the at least partially compressed prosthetic valve with a flared portion of the nose cone, and re-positioning the prosthetic valve while the distal end portion of the at least partially compressed prosthetic valve is covered by the flared portion of the nose cone.

In some embodiments, the method can further comprise re-expanding the prosthetic valve from the at least partially compressed state to the radially expanded state. In some embodiments, the method can further comprise after re-expanding the prosthetic valve, releasing the prosthetic valve from the delivery apparatus and positioning a sheath of the delivery apparatus over the flared portion of the nose cone to cause the flared portion to fold in a distal direction. In some embodiments, re-positioning the prosthetic valve can comprise crossing the native aortic valve.

The foregoing and other objects, features, and advantages of the invention will become more apparent from the following detailed description, which proceeds with reference to the accompanying figures.

BRIEF DESCRIPTION OF THE DRAWINGS

FIG. 3-5 are various views of an exemplary expansion mechanism and portions of the frame of the prosthetic heart valve of FIG. 1.

FIG. 6 is a perspective view of the expansion mechanism of FIGS. 3-5.

FIG. 7 is another perspective view of the expansion mechanism of FIG. 6 showing the radial outer surface of the expansion mechanism.

FIG. 9 is a perspective view of the expansion mechanism of FIG. 6 showing hidden components in dashed lines.

FIG. 10 is a side elevation view of the expansion mechanism of FIG. 6.

FIG. 11 is a cross-sectional view of the expansion mechanism taken along line 11-11 of FIG. 7.

FIG. 17 shows a schematic view of another exemplary expansion mechanism that can be used with the prosthetic heart valve of FIG. 2.

FIG. 18 shows a schematic diagram of another exemplary embodiment of an expansion mechanism that can be used with the prosthetic heart valve of FIG. 2.

FIG. 21 is a cross-sectional view of an exemplary nose cone that can be used in a delivery apparatus for delivering a prosthetic heart valve, such as the prosthetic heart valve of FIG. 2.

FIGS. 22A-22D are side views of the distal end portion of an exemplary delivery apparatus incorporating the nose cone of FIG. 21.

DETAILED DESCRIPTION

Figure 1:
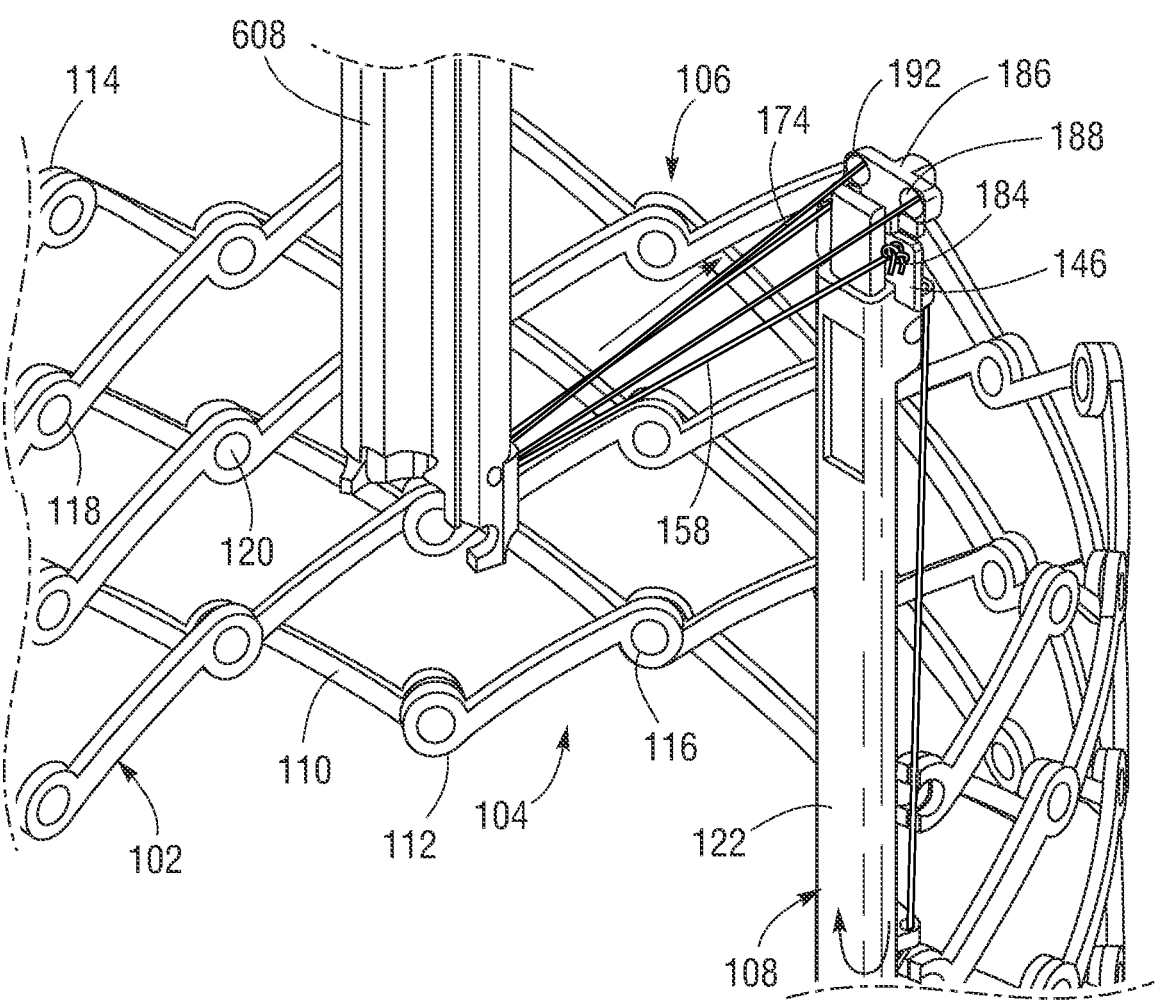
FIG. 1 shows a portion of an exemplary embodiment of a prosthetic heart valve.
Figure 2:
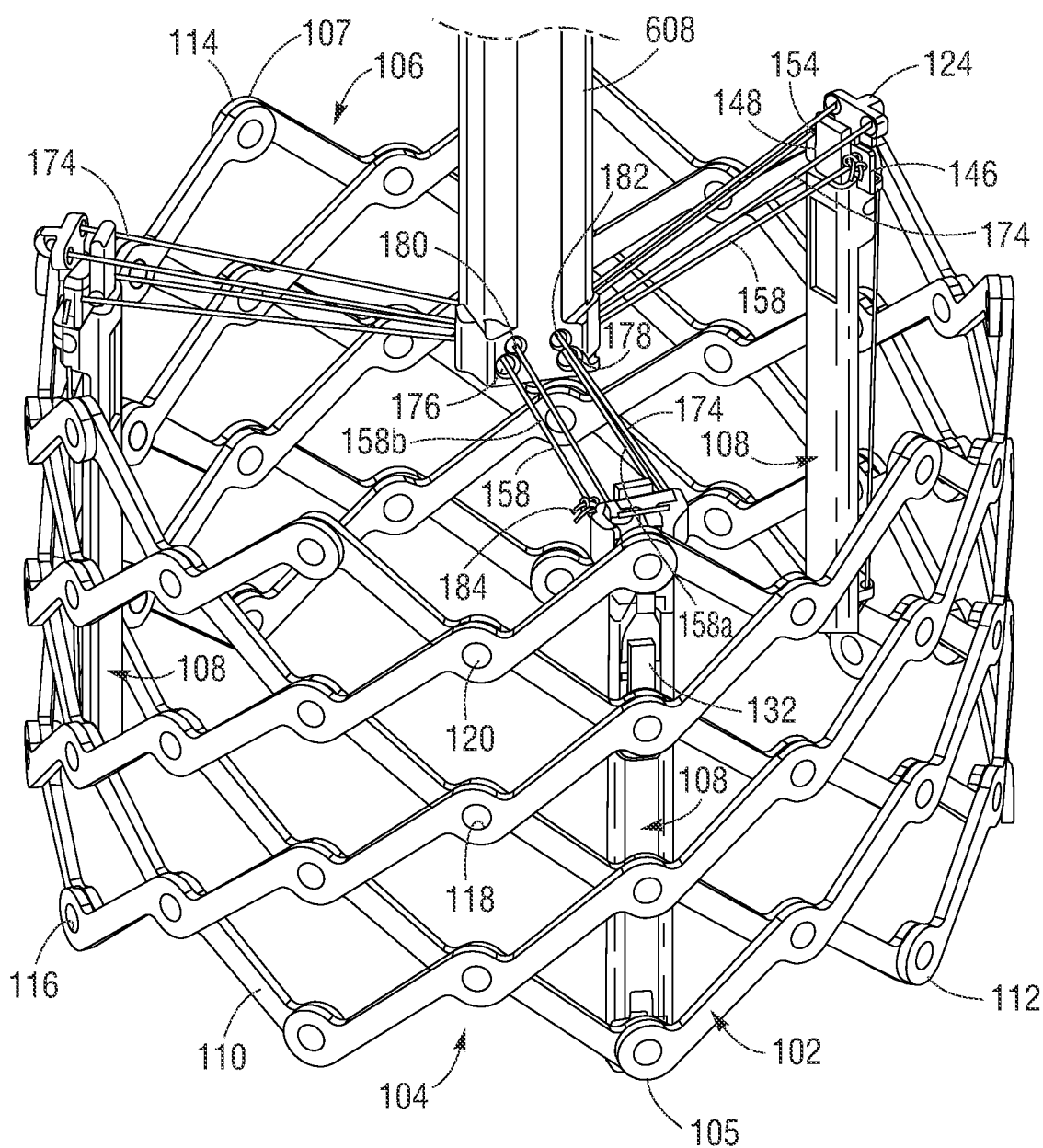
FIG. 2 shows a perspective view of the prosthetic heart valve of FIG. 1 and the distal end portion of a delivery apparatus coupled to the prosthetic heart valve.
Figure 8:
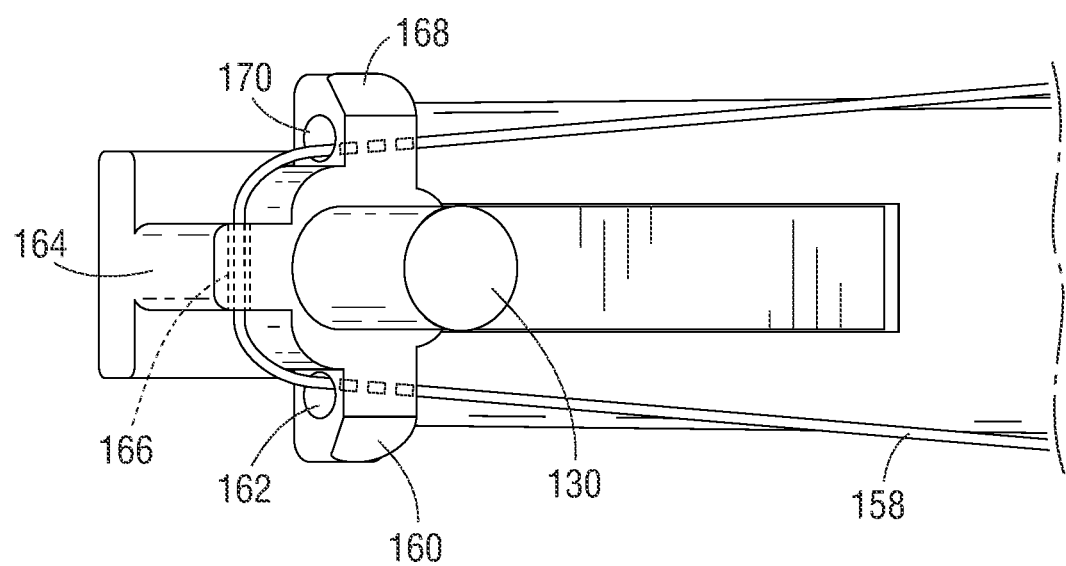
FIG. 8 is an enlarged view of one end portion of the expansion mechanism of FIG. 6.

FIGS. 1-2 show various views of a prosthetic heart valve 100, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 100 can comprise a stent or frame 102, a valvular structure (not shown), and one or more expansion mechanisms 108. In the illustrated example, the prosthetic valve 100 includes three such expansion mechanisms 108 positioned equidistant from each other around the circumference of the frame 102. In other embodiments, there can be more or less than three expansion members. The valvular structure can comprise three leaflets, which can form a leaflet structure and be arranged to collapse in a tricuspid arrangement.

The frame 102 can comprise an inflow end portion 104 defining a frame inflow end 105 and an outflow end portion 106 defining a frame outflow end 107. The prosthetic valve 100 can define a longitudinal axis extending through the inflow end portion 104 and the outflow end portion 106. The expansion mechanisms 108 can be configured to radially expand and compress the frame 102, as discussed more fully below.

The frame 102 can be made of any of various suitable materials, such as stainless steel or a nickel titanium alloy ("NiTi"), for example Nitinol. The frame 102 can include a plurality of interconnected struts 110 arranged in a lattice-type pattern and forming a plurality of apices 112 at the inflow end 105 of the frame 102. The frame 102 can include similar apices 114 at the outflow end 107 of the frame 102. The struts 110 are shown as positioned diagonally, or offset at an angle relative to, and radially offset from, the longitudinal axis of the prosthetic valve 100. In other implementations, the struts 110 can be offset by a different amount than depicted in FIGS. 1-2, or some or all of the struts 110 can be positioned parallel to the longitudinal axis of the prosthetic valve 100.

The struts 110 can be pivotably coupled to one another. In the illustrated embodiment, for example, the end portions of the struts 110 forming the apices 112 at the inflow end 105 and the apices 114 at the outflow end 107 of the frame 102 can have a respective opening or aperture 116. The struts 110 also can be formed with openings or apertures 118 spaced apart along their lengths between the opposite ends of the struts. Respective hinges can be formed at the apices 112 and at the junctions/locations where struts 110 overlap each other between the ends of the frame via fasteners 120, which can comprise rivets or pins that extend through the apertures 116, 118. The hinges can allow the struts 110 to pivot relative to one another as the frame 102 is radially expanded or compressed, such as during assembly, preparation, or implantation of the prosthetic valve 100. For example, the frame 102 (and thus the prosthetic valve 100) can be manipulated into a radially compressed or contracted configuration (see, e.g., FIG. 13) and inserted into a patient for implantation. Once inside the body, the prosthetic valve 100 can be manipulated into an expanded state (see, e.g., FIG. 2) and then released from the delivery apparatus, as further described below.

The frame 102 can be formed using any suitable technique. Suitable techniques can include separately forming individual components (e.g., the struts 110 and fasteners 120) of the frame and then mechanically assembling and connecting the individual components to form the frame 102. The struts 110 and fasteners 120 can be formed, for example, by laser cutting those components from sheets or tubes of metal, or by electroforming (electroplating or electrodeposition) or physical vapor deposition. In some embodiments, electroforming or physical vapor deposition can be used to form subcomponents of the frame 102 or the entire frame 102 with pivotable connections between the struts 110. In one implementation, for example, electroforming or physical vapor deposition can be used to form struts 110 having integral fasteners 120. The individual struts 110 can be assembled together into a frame by inserting the integral fasteners 120 of each strut through a corresponding aperture of an adjacent strut. In some embodiments, electroforming or physical vapor deposition can be used to form the entire frame 102 in its final, cylindrical shape. In other embodiments, electroforming or physical vapor deposition can be used to form the entire frame in a flattened configuration, after which the ends of the flattened frame are connected to each other to form the final cylindrical shape of the frame.

In other embodiments, the struts 110 are not coupled to each other with respective hinges (e.g., fasteners 120) but are otherwise pivotable or bendable relative to each other to permit radial expansion and compression of the frame 102. For example, the frame 102 can be formed (e.g., via laser cutting, electroforming or physical vapor deposition) from a single piece of material (e.g., a metal tube). Further details regarding the construction of the frame 102 are disclosed in U.S. Patent Publication No. 2018/0153689 and U.S. application Ser. No. 15/995,528, filed Jun. 1, 2018, which are incorporated herein by reference in their entirety.

Further details regarding transcatheter prosthetic heart valves, including the manner in which the valvular structure can be coupled to the frame 102 of the prosthetic valve 100, can be found, for example, in U.S. Pat. Nos. 6,730,118, 7,393,360, 7,510,575, 7,993,394, and 8,652,202, and U.S. application Ser. No. 15/978,459, filed May 14, 2018, which are incorporated herein by reference in their entireties.

Figure 13:
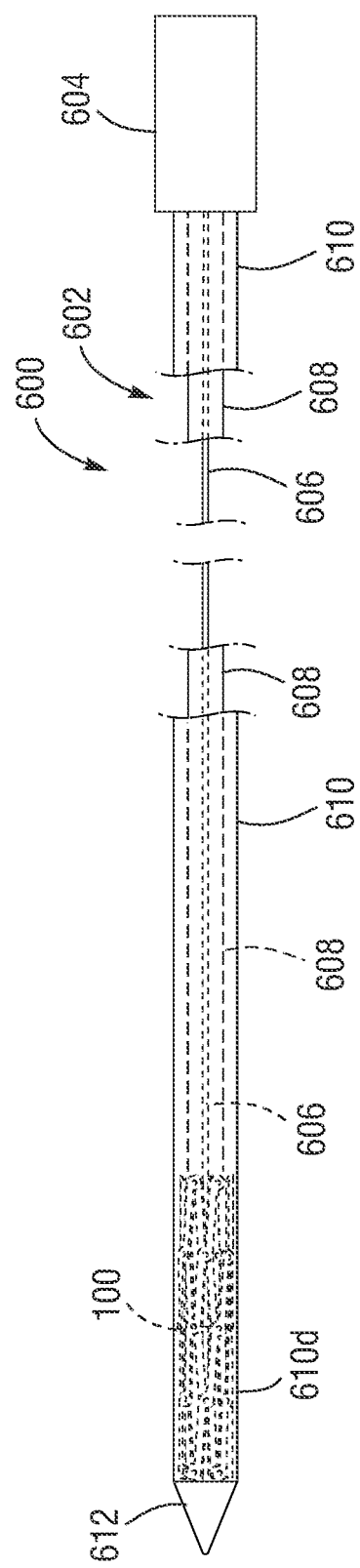
FIG. 13 is a side elevation view of an exemplary delivery apparatus that can be used to deliver and implant the prosthetic heart valve of FIG. 2.

FIG. 2 shows the prosthetic valve 100 releasably connected to the distal end portion of a positioning member 608 of a delivery apparatus. FIG. 13 shows one example of a delivery assembly 600 that can be used to deliver and implant any of the prosthetic valves disclosed herein within a patient's body. The delivery assembly 600 can include two main components: a delivery apparatus 602 and a prosthetic heart valve, such as prosthetic heart valve 100. The prosthetic valve 100 can be mounted in a radially compressed configuration around a distal end portion of the delivery apparatus 602 for insertion into a patient's body. In some embodiments, the prosthetic valve 100 can be oriented so that the outflow end is positioned proximally relative to the inflow end. In this orientation, the prosthetic valve can be advanced through the patient's vasculature in a retrograde approach (e.g., through a femoral artery and the aorta) to the heart for implantation at the native aortic valve. In other embodiments, the prosthetic valve 100 can be oriented so that the inflow end is positioned proximally relative to the outflow end, depending on the particular delivery approach used and the implantation location for the prosthetic valve.

The delivery apparatus 602 in the illustrated embodiment includes a handle 604, a first shaft 606, a positioning member in the form of a second shaft 608 extending co-axially over the first shaft 606, a third shaft 610 extending co-axially over the second shaft 608, and a nose cone 612. The first shaft 606 is the inner-most shaft in the illustrated embodiment and can be referred to as the inner shaft of the delivery apparatus 602. Likewise, the third shaft 610 is the outer-most shaft in the illustrated embodiment and can be referred to as the outer shaft or outer sheath of the delivery apparatus 602. The shafts 606, 608, 610 can be axially and/or rotationally moveable relative to each other.

The nose cone 612 can be connected to a distal end of the inner shaft 606. A guide wire (not shown) can extend through a central lumen of the inner shaft 606 and an inner lumen of nose cone 612, so that the delivery apparatus 602 can be advanced over the guide wire inside the patient's vasculature.

The proximal ends of the shafts 606, 608, 610 can be coupled to the handle 604. During delivery of a prosthetic valve, the handle 604 can be maneuvered by a surgeon to advance or retract the delivery apparatus through the patient's vasculature. In some embodiments, the handle 604 can include a plurality of knobs or other actuating mechanisms for controlling different components of the delivery apparatus 602 in order to expand and/or deploy the prosthetic valve. For example, the handle 604 can include one or more knobs or other actuating mechanisms, each configured to produce relative axial and/or rotational movement of a selected shaft 606, 608, or 610 relative to the others.

As further shown in FIG. 13, a distal end portion 610d of the outer sheath 610 can extend over the prosthetic valve 100 and contact the nose cone 612 in the delivery configuration of the delivery apparatus 602. Thus, the distal end portion 610d of the outer sheath 610 can serve as a delivery capsule that contains or houses prosthetic valve 100 in the radially compressed configuration for delivery through the patient's vasculature. The outer sheath 610 and the inner shaft 606 can be configured to be axially movable relative to one another such that proximal movement of the outer sheath 610 relative to the inner shaft 606 (or distal movement of the inner shaft 606 relative to the outer sheath 610) can expose the prosthetic valve 100 from the outer sheath 610. In alternative embodiments, the prosthetic valve 100 need not be housed within the outer sheath 610 during delivery. As such, in some embodiments, the delivery apparatus 602 does not include the outer sheath 610.

Figure 12:
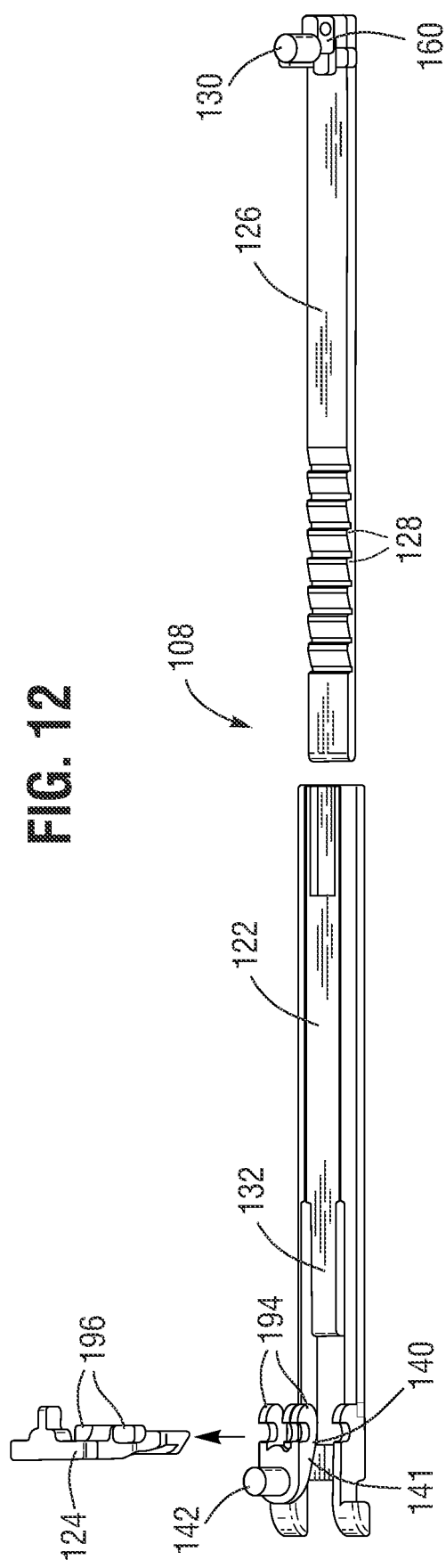
FIG. 12 is an exploded, perspective view of the expansion mechanism of FIG. 6.

As best shown in FIGS. 9 and 12, each expansion mechanism 108 in the illustrated embodiment can comprise a housing 122, a first expansion member 124, and a second expansion member 126. The first expansion member 124 can be secured to the frame 102 at a first location and the second expansion member 126 can be secured to the frame at a second location, axially spaced from the first location. Further, the first expansion member 124 and the second expansion member 126 can be axially moveable within the housing 122 with respect to each other. As such, because the first and second expansion members 124, 126 are secured to the frame 102 at axially spaced locations, moving the first and second expansion members axially with respect to each other in a telescoping manner can cause the frame to radially expand or compress depending on which direction the expansion members move.

For example, in the illustrated embodiment, the first expansion member 124 is secured to the frame 102 near the outflow end 107 and the second expansion member 126 is secured to the frame near the inflow end 105. As such, moving the second expansion member towards the outflow end of the frame while holding the first expansion member in a fixed position can cause the frame to foreshorten axially and expand radially.

In the illustrated example, the expansion mechanism 108 comprises a ratchet mechanism or ratchet assembly, wherein the second expansion member 126 comprises a linear rack having a plurality of teeth 128 and the first expansion member 124 comprises a pawl configured to engage with the teeth of the linear rack. The pawl 124 and the rack 126 are configured such that when the pawl is engaged with the rack, movement between the pawl and the rack is possible in one axial direction but is prohibited in the opposite axial direction. In the illustrated example, as best shown in FIGS. 4 and 11, when the pawl 124 is engaged with the rack 126, the rack can move in one axial direction (up in the orientation of FIG. 4) but cannot move in the opposite axial direction (down in the orientation of FIG. 4). This ensures that while the pawl 124 is engaged with the rack 126, the frame 102 can be radially expanded but cannot be radially compressed. Thus, after the prosthetic valve 100 is implanted in a patient, the frame 102 can be expanded to a desired diameter based on the patient's anatomy, as described herein.

Once the desired diameter for the prosthetic valve is reached, the delivery apparatus used to implant the valve 100 can be disconnected from the prosthetic valve removed from the patient, leaving the prosthetic valve implanted in the patient. The patient's native anatomy (e.g., the native aortic annulus) may exert radial forces against the prosthetic valve that would tend to compress the frame 102. However, the engagement between the pawl 124 and the rack 126 prevents such forces from compressing the frame 102, thereby ensuring that the frame remains locked in the desired radially expanded state. The pawl 124 can be configured to be selectively disengaged from the rack 126 by a user to permit radial compression of the frame if repositioning or recapture and removal of the prosthetic valve is desired, as further described below.

Referring to FIGS. 4-5 and 11, the linear rack 126 can comprise an elongated bar that extends through the housing 122. As can best be seen in FIG. 3, the housing 122 can be open at one end (e.g., the end closest to the outflow end 107 of the frame) such that the rack 126 can extend through the housing and beyond the end of the housing. In another example, the housing 122 can be closed at this end. In the illustrated example, a portion of the rack 126 near the outflow end 107 of the frame 102 comprises a plurality of teeth 128. In other examples, substantially the entire length of the rack 126 can comprise teeth 128.

The rack 126 can be secured to the frame 102 near the inflow end 105. In the illustrated example, the rack 126 comprises a post 130 at one end that can be used to secure the rack to the frame 102. The post 130 can be configured to extend through openings 116 in two struts 110 at an apex 112 of the frame 108. As such, when the rack 126 is moved axially within the housing 122, the post 130 moves along with the rack, thereby causing the portion of the frame to which the post is attached to move axially as well, which causes the frame 102 to foreshorten axially and expand radially. The struts 110 to which the post 130 is connected are free to pivot relative to the post and to one another as the frame is expanded or compressed. In this manner, the post 130 serves as the fastener that forms the pivotable connection between those struts.

In other embodiments, the post 130 can be connected to the intersection of two struts 110 at a location offset from the inflow end 105 of the frame. In alternative embodiments, the rack 126 need not include post 130 and instead can be mounted to a fastener 120 or at another convenient location on the frame.

Referring to FIGS. 4-9 and 11, the pawl 124 can comprise an engagement portion 134, an intermediate portion 136, and a release portion 138. The engagement portion 134 can comprise a finger-like member terminating in a tooth 135 that can engage the teeth 128 of the rack 126. The tooth 135 can have a shape that is complimentary to the shape of the teeth 128, such that the tooth 135 allows sliding movement of the rack 126 in one direction relative to the pawl 124 (upward in the illustrated embodiment) and resists sliding movement of the rack 126 in the opposite direction (downward in the illustrated embodiment) when the tooth 135 is in engagement with one of the teeth 128 of the rack.

The intermediate portion 136 of the pawl can be coupled to a coupling member 140, which in turn can be secured to the frame 102. The release portion 138 can extend radially outward and away from the rack 126 when the engagement portion 134 is engaged with the teeth 128 of the rack 126, as shown in FIG. 4. The coupling member 140 can be configured to form a pivotable connection with the pawl 124 that fixes the axial position of the pawl relative to the frame 102 yet allows the pawl 124 to pivot relative to the frame 102 and the rack 126 so that the pawl can pivot into and out of engagement with the rack. In the illustrated configuration, as best shown in FIGS. 6-7, the coupling member 140 can comprise an inner body portion 141 and a post 142 extending radially outwardly from the inner body portion 141. The inner body portion 141 can be formed with one or more ears 194 (e.g., first and second spaced apart ears 194 in the illustrated embodiment) configured to receive a respective pivot element of the pawl 124.

The post 142 can extend through apertures 116 of two overlapping struts 110 that form an apex 114 at the outflow end 107 of the frame. The struts 110 to which the post 142 is connected are free to pivot relative to the post and to one another as the frame is expanded or compressed. In this manner, the post 142 serves as the fastener that forms the pivotable connection between those struts.

In other embodiments, the post 142 can be connected to the intersection of two struts 110 at a location offset from the outflow end 107 of the frame. In alternative embodiments, the coupling member 140 need not include post 142 and instead can be mounted to a fastener 120 or at another convenient location on the frame.

The intermediate portion 136 of the pawl 124 can include one or more pivot elements 196 (two in the illustrated embodiment) received in corresponding notches or openings in the ears 194 of the coupling member 140. The connection of the pivot elements 196 with the ears 194 allows the pawl 124 to pivot relative to the coupling member 140 and the rack 126 about an axis 198 (FIG. 7) extending through the pivot elements. Moreover, the ears 194 can be shaped to retain the pivot elements 196 therein, thereby fixing the axial position of the pawl 124 relative to the frame 102.

As best shown in FIG. 5, the inner body portion 141 of the coupling member can include a rounded or curved inner surface 144 that engages an adjacent outer surface 198 of the intermediate portion 136 of the pawl. The outer surface 198 can be rounded or curved to correspond with the shape of the inner surface 144 of the coupling member 140 to facilitate the rocking or pivoting motion of the pawl 124 relative to the coupling member 140. When an inwardly directed radial force is applied to the release portion 138 of the pawl 124, the pawl pivots relative to the axis 198 with the release portion 138 moving radially inwardly and the engagement portion 134 moving radially outwardly such that the tooth 135 is disengaged from the teeth 128 of the rack 126 (as best shown in FIG. 5). Once the pawl 124 disengages from the rack 126, the rack is free to move through the housing 122 in either axial direction. This can be useful if radial compression of the frame is desired during an implantation procedure, as described in further detail below.

Referring again to FIGS. 4-9 and 11, the housing 122 can comprise a retaining member 132 configured to resiliently retain the pawl 124 in a position engaging the rack 126 (which can be referred to as the locked position). The retaining member 132 can be a flexible and resilient portion of the housing 122 that extends over and contacts a radial outer surface of the engagement portion 134 of the pawl 124. In the illustrated embodiment, the retaining member 132 is in the form of a leaf spring that can be integrally formed with the housing or separately formed and subsequently connected to the housing.

The retaining member 132 can apply a radial inwardly directed biasing force against the engagement portion 134 of the pawl 124. This ensures that under normal operation, the pawl 124 stays engaged with the teeth 128 of the rack 126 unless the user performs an unlocking step to remove the pawl 124 from engagement with the rack 126 against the bias of the retaining member 132, as further described below. Thus, once the prosthetic valve 100 is expanded to a diameter in which the pawl 124 can engage a tooth 128 of the rack, the prosthetic valve 100 is retained in a normally locked configuration, where the prosthetic valve can be further expanded but cannot be collapsed. However, the retaining member 132 is flexible enough such that a radially inwardly directed force applied to the release portion 138 by a user can overcome the biasing force of the retaining member 132 to permit pivoting of the engagement portion 134 of the pawl away from the rack.

As generally shown in FIGS. 1 and 2, each expansion mechanism 108 can be provided with an expansion cord 158 to produce radial expansion of the frame 102 and a release cord 174. Each expansion cord 158 is operatively connected to the rack 126 of a corresponding expansion mechanism 108 and to a delivery apparatus (e.g., delivery apparatus 602) which can have actuator(s) that can selectively increase and decrease the tension applied to the expansion cord, thereby controlling the expansion of the frame 102. Increasing tension on an expansion cord 158 is effective to produce axial movement of the rack 126 relative to the pawl 124 to radial expand the frame 102.

Each release cord 174 is operatively connected to the pawl 124 of a corresponding expansion mechanism 108 and to a delivery apparatus (e.g., delivery apparatus 602) which can have actuator(s) that can selectively increase and decrease the tension applied to the release cord, thereby controlling the position of the pawl 124 relative to the rack 126. Increasing tension on a release cord 174 is effective to pivot the pawl 124 in a first direction whereby the release portion 138 of the pawl 124 is pulled radially inwardly while the engagement portion 134 moves away from the rack (FIG. 5) against the bias of the retaining member 132. Decreasing or releasing tension on the release cord 174 allows the pawl to pivot in a second direction, opposite the first direction, under the bias of the retaining member 132, which causes the engagement portion 134 of the pawl 124 to engage the rack 126.

Furthermore, in certain embodiments, the radial inward force of multiple cords 174 acting on the frame 102 through the pawls 124 is effective to collapse the frame 102. Explaining further, when at least two of the cords 174 are tensioned in the proximal direction, the cords apply radially inwardly directed forces at two circumferentially spaced locations on the frame via the pawls 124. The radial forces pull the struts inwardly and begin collapsing the frame. Due to the rigidity of the struts 110 and the pivotable connections between the struts, the radial forces cause the entire frame 102 to collapse. Thus, the cords 174 in the illustrated embodiment serve two functions, namely, "unlocking" the frame 102 by disengaging the pawls from their respective racks and collapsing the frame once the pawls are disengaged from the respective racks.

In particular embodiments, the expansion cords 158 and the release cords 174 can comprise any flexible pieces of material that can be routed through the openings of the expansion mechanism and placed in tension to produce movements of the rack 126 and the pawl 124 as described herein. In the present disclosure, a cord 158, 174 can be, for example, a suture (e.g., a single filament suture or a multi-filament suture), a wire (e.g., a metal wire formed from stainless steel, Nitinol or other suitable metals), a cable (e.g., a braided cable formed from metal or polymeric strands) or any other similar materials that can be threaded through the expansion mechanism and placed in tension as described herein.

As best seen in FIGS. 6-7, the upper portion of the housing 122 can further comprise a first cord receiving member 146 and a second cord receiving member 148. The first and second cord receiving members 146, 148 can be positioned near the outflow end 106 of the frame 102 on either side of the expansion mechanism 108. The first cord receiving member 146 can comprise a first radial opening 150, oriented in a radial direction, as best seen in FIG. 3, and a first axial opening 152, oriented in an axial direction, as best seen in FIGS. 6-7, which is in communication with the opening 150 to form a first passage through the first cord receiving member. The second cord receiving member 148 can comprise a second radial opening 154, oriented in a radial direction, as best seen in FIG. 2, and a second axial opening 156, oriented in an axial direction, as best seen in FIG. 7, which is in communication with the opening 154 to form a second passage through the second cord receiving member. The first and second cord receiving members 146, 148 can be configured to receive an expansion cord 158 through the openings 150, 152, 154, 156, which can be used to expand the prosthetic valve 100, as explained in further detail below.

As best seen in FIGS. 6-9, the lower end portion of the rack 126 can include a cord routing member 160. The post 130 can extend radially outwardly from the cord routing member 160. The member 160 can comprise a first opening or passage 162 oriented in an axial direction, a second opening or passage 166 oriented in a circumferential direction, and a third opening or passage 170 oriented in an axial direction. The first, second, and third openings 162, 166, 170 are configured to receive the expansion cord 158 as discussed in further detail below.

Figure 15:
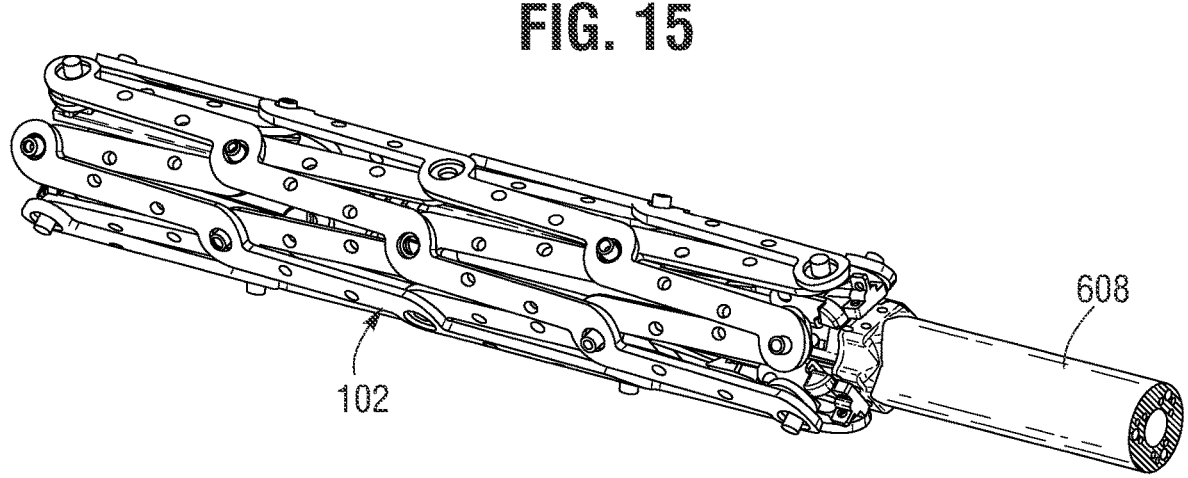
FIGS. 15-16 show the prosthetic heart valve of FIG. 2 in a radially collapsed configuration and coupled to the distal end portion of a delivery apparatus.
Figure 16:
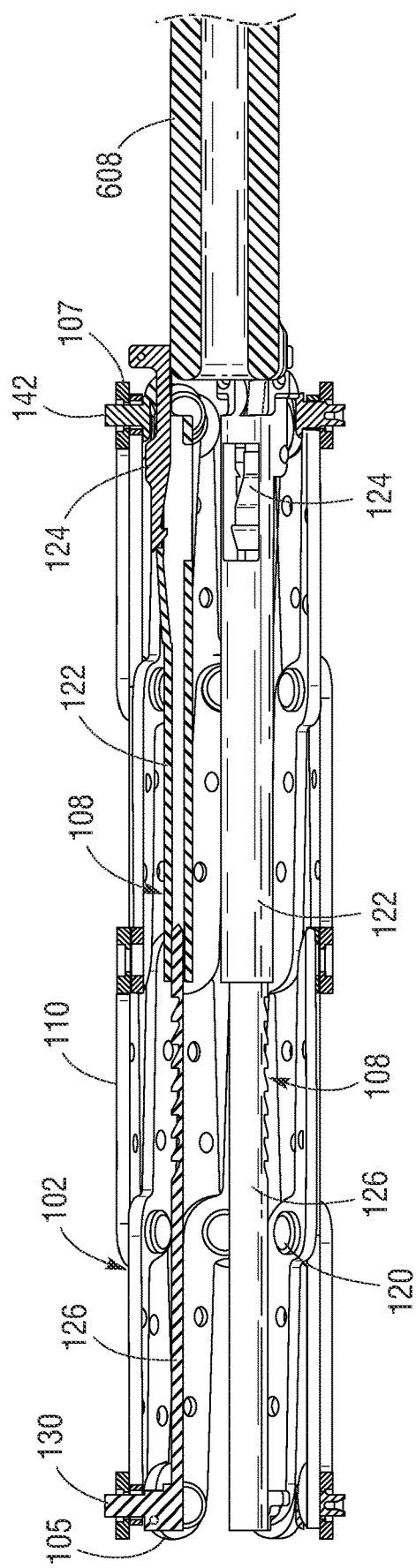

As best shown in FIGS. 1-2, the expansion cord 158 and release cord 174 from each expansion mechanism 150 can extend proximally through the positioning member 608 of the delivery apparatus. During an implantation procedure, the positioning member 608 can be positioned and oriented along the central longitudinal axis of the frame 102. FIGS. 15-16 show the positioning member 608 and the frame 102 when the frame is in a radially collapsed state. The expansion cords 158 and/or the release cords 174 can be used to releasably connect the prosthetic valve to the positioning member 608 during delivery and deployment of the prosthetic valve 100. After the prosthetic valve 100 has been expanded at the desired implantation site within the patient's body, the cords 158, 174 can be removed from the prosthetic valve 100 and the delivery apparatus can be removed from the patient's body, as further described below.

Referring again to FIG. 2, the positioning member 608 can comprise a plurality of openings to receive the expansion cord 158 and a release cord 174 from each expansion mechanism 108. The positioning member 608 can be formed with a set of openings on each face or surface portion of the positioning member facing a corresponding expansion mechanism 108. Each set of openings can comprise a first opening 176 and a second opening 178 to receive the expansion cord 158, and a third opening 180 and a fourth opening 182 to receive the release cord 174 from the corresponding expansion mechanism 108. The first and second openings 176, 178 can be spaced apart from each other and the third and fourth openings 180, 182 similarly can be spaced apart from each other at locations above (proximal) the first and second openings. With the third and fourth openings 180, 182 positioned above and slightly offset from the first and second openings 176, 178, the expansion cord 158 and the release cord 174 can both be threaded through the positioning member 608 without interfering with each other.

As best shown in FIG. 2, in the illustrated example, where the prosthetic valve 100 comprises three expansion mechanisms 108, the distal end portion of the positioning member 608 comprises three faces or surface portions oriented parallel to each of the expansion mechanisms 108. Each face of the positioning member can comprise a set of four openings similar to openings 176, 178, 180, 182 such that each face can receive an expansion cord and a release cord from one of the expansion mechanisms 108. Each opening 176, 178, 180, 182 in a set of openings can be in communication with a respective lumen extending through the positioning member 608. The remainder of this disclosure sometimes references one expansion cord 158, one release cord 178 and one side of the positioning member 608. However, it should be understood that the disclosure can apply to additional expansion mechanisms and additional sides of the positioning member 608.

As best shown in FIGS. 2, 6, and 7, each expansion cord 158 can form a long loop having proximal ends at the handle 604 and which extends distally from the handle 604 through the positioning member 608 and is routed through a corresponding expansion member. More specifically, starting at the handle 604, each expansion cord 158 extends longitudinally through the positioning member 608 (e.g., through a lumen of the positioning member), outwardly through the first opening 176, through the openings 150, 152 in first cord receiving member 146 of the housing 122, longitudinally along one side of the expansion mechanism 108, through the openings 162, 166, 170 in the cord routing member 160 of the rack 126, longitudinally along the other side of the expansion mechanism, through the openings 154, 156 in the second cord receiving member 148, inwardly through the second opening 178 in the positioning member 608 and longitudinally back through the positioning member 608 (e.g., through a lumen of the positioning member) to the handle 604 of the delivery apparatus. For ease of description, the section of the loop extending from the expansion mechanism back to the handle 604 is labeled with reference number 158a and the section of the loop extending from the handle 604 to the expansion mechanism is labeled with reference number 158b.

One or both of the proximal ends of the loop sections 158a, 158b can be operatively connected to a respective actuator (e.g., a knob) on the handle 604 that can be used to adjust the tension in the cord 158. In one embodiment, for example, the proximal end of loop section 158a of each expansion cord 158 can be operatively connected to a respective actuator that is operable to adjust the tension of a respective expansion cord, allowing the user to selectively adjust the tension of individual expansion cords 158. In other embodiments, the proximal ends of plural loop sections 158a can be operatively connected to the same actuator that is operable to adjust the tension of each expansion cord simultaneously. As will be further explained below, expansion of the prosthetic valve 100 can be accomplished by tensioning or applying a proximally directed force to the proximal ends of loop sections 158a while the proximal ends of loop sections 158b remain fixed relative to the delivery apparatus. In such cases, the proximal ends of loop sections 158b can be fixed at any convenient locations on the delivery apparatus. For example, the proximal ends of loop sections 158b can be secured inside the handle 604 of the delivery apparatus.

As best shown in FIGS. 1-2, each expansion cord 158 can include a stop member, for example, in the form of a knot 184 positioned between the expansion mechanism 108 and the positioning member 608. In the illustrated example, the knot 184 is positioned between the first radial opening 150 in the first cord receiving member 146 and the first opening 176 in the positioning member 608. The knot 184 can be sized such that it cannot pass through the opening 150. In the illustrated example, the knot 184 can be formed from a separate piece of cord (e.g., suture material) that is tied or knotted around the expansion cord 158.

In other examples, the knot 184 can be formed by forming a knot directly in the expansion cord 158. In still other examples, instead of a knot 184, the stop member can comprise a piece of material affixed to the expansion cord 158 and sized such that it cannot pass through the opening 150. For example, stop member can comprise a bead or bead-like member, such as a small spherical bead, and the expansion cord can pass through a bore extending completely through the bead, which is fixed longitudinally to the expansion cord such that the bead cannot move along the length of the cord. The knot 184 (or other stop member) functions to apply a counter force against the expansion mechanism 108 during frame expansion, as explained in further detail below.

To expand the frame 102, the proximal end of the cord section 158a is pulled by a physician at a proximal end of the delivery apparatus 602 either directly or via an actuator on the handle 604. As tension on the expansion cord 158 is increased, the knot 184 prevents the cord section 158b from being pulled through the opening 150 in the housing 122. Thus, as a proximal force is applied to the cord section 158a, the cord is pulled through the cord routing member 160 while applying a proximally directed force against the cord routing member 160, and thereby pulling the rack 126 in the proximal direction relative to the housing 122 and the pawl 124 toward the outflow end of the frame 102. Because the rack 126 is fixed to the frame 102 at one location and the pawl 124 is fixed to the frame 102 at another location (via coupling member 140), moving of the rack 126 is effective to produce radial expansion of the frame. In examples where the prosthetic valve 100 comprises multiple expansion mechanisms 108 (e.g., three expansion mechanisms), the prosthetic valve can be radially expanded by simultaneously pulling on the expansion cord associated with each expansion mechanism. Routing the expansion cord 158 through or around a cord routing member on the rack 126 provides a 2:1 mechanical advantage for moving the rack relative to the pawl (similar to a moving pulley system), thereby significantly reducing the amount of force required to radial expand the prosthetic valve.

As the rack 126 moves with respect to the pawl 124, the tooth 135 engages successive teeth 128 of the rack, with each tooth 128 representing a different degree of radial expansion of the prosthetic valve. The teeth 128 and the tooth 135 are shaped to allow the teeth 128 to pass over tooth 135 as the rack moves into the housing (in the proximal direction in the illustrated embodiment) to allow the prosthetic valve to expand but the engagement of the tooth 135 with one of the teeth 128 resists movement of the rack in the opposite direction. The retaining member 132 ensures that the tooth 135 of the pawl 124 remains engaged with the teeth 128 of the rack 126.

Once a desired expansion level of the prosthetic valve 100 is reached, a user can remove the expansion cords 158 from the expansion mechanisms 108 by disconnecting the proximal ends of loop sections 158a from their respective actuator(s) on the handle (if they are connected to actuator(s)) and pulling loop sections 158b in the proximal direction. This causes the proximal ends of loop sections 158a to be pulled through their respective expansion mechanisms 108 and into openings 176 of the positioning member 608 of the delivery apparatus, effectively freeing the prosthetic valve from the expansion cords 158. The openings 176 can be sized such that the knots 184 can pass through the openings 176 into the positioning member 608 as the user pulls the proximal ends of loop sections 158b.

If the prosthetic valve 100 needs to be radially compressed during an implantation procedure (e.g., if the prosthetic valve was over-expanded or if the prosthetic valve needs to be repositioning or recaptured and removed from the patient), the release cords 174 can be used, as described herein. Similar to the expansion cords 158, each release cord 174 can be an elongated loop that extends distally from the handle, through the delivery apparatus and around a portion of an expansion mechanism 108.

The release portion 138 of each pawl 124 can include a cord routing member 186 through which a release cord 174 extends. The routing member can include a first opening 188, oriented in a radial direction, a second opening 190, oriented in a circumferential direction, and a third opening 192, oriented in a radial direction.

Referring to FIGS. 2 and 3, starting at the handle, each release cord 174 extends longitudinally through the positioning member 608 (e.g., through a lumen of the positioning member), outwardly through the third opening 180 of the positioning member 608 (as best shown in FIG. 2), through openings 188, 190, 192 of a cord routing member 186 of a corresponding expansion mechanism 108 (effectively looping around the pawl 124), inwardly through the fourth opening 182 of the positioning member and longitudinally back through the positioning member 608 (e.g., through a lumen of the positioning member) to the handle 604 of the delivery apparatus.

One or both ends of the loop formed by each release cord 174 can be exposed at the proximal end of the delivery apparatus so that they can be manipulated by a user. Alternatively, both ends of each release cord can be operatively connected to a respective actuator that is operable to increase and decrease tension applied to each release cord. In alternative embodiments, the ends of each release cord 174 can be operatively connected to a common actuator that is operable to simultaneously increase and decrease tension applied to all of the release cords.

In any case, applying a proximally directed force to the ends of a release cord 174 (either by manually pulling the ends or actuating an actuator) is effective to pull the release portion 138 of a corresponding pawl 124 radially inwardly. This causes the pawl 124 to pivot relative to the pivot axis 198 such that the tooth 135 pivots away from and disengages from the teeth 128 of the rack 126. This unlocks the expansion mechanism 108 and allows the frame 102 to be radially compressed.

If the release cords 174 are further tensioned, the release portions 138 of the pawls 124 will exert an inwardly directed radial force against the outflow end portion 106 of the frame 102, which radially compresses the frame (and therefore the prosthetic valve). Once the frame 102 is compressed a desired amount, the pulling forces applied to the release cords 174 can be released, which allows the biasing force of the retaining members 132 force the teeth 135 of the pawls 124 back into engagement with their respective racks 126, effectively placing the expansion mechanisms 108 in their locked states to prevent further radial compression of the frame. If desired, the prosthetic valve 100 can be repositioned within the patient's body or fully compressed and removed from the patient's body. If the prosthetic valve is repositioned, the user can re-expand the prosthetic valve by actuating the expansion cords 158 as previously described.

Once the prosthetic valve is expanded to a selected diameter at the desired implantation position, the user can remove the release cords 174 from the prosthetic valve by pulling on one end of each release cord 174 in the proximal direction. This will cause the opposite end of each release suture 174 to be pulled through the cord routing member 186 of the corresponding pawl 124 and back into the positioning member 608 of the delivery apparatus. Removing each release cord 174 and each expansion cord 158 as previously described effectively disconnects the prosthetic valve from the delivery apparatus, after which the delivery apparatus can be removed from the patient's body.

In alternative embodiments, an expansion mechanism 108 can be actuated with an expansion cord 158 that is not looped through the rack 126. For example, an expansion cord can have a distal end secured to the rack 126 at any convenient location and a proximal end of the expansion cord can be exposed at the proximal end of the delivery apparatus or connected to the handle 604. In this manner, applying a proximally directed force on the proximal end of the expansion cord pulls the rack 126 relative to the pawl 124 in order to expand the frame 102, although without a mechanical advantage.

It should be noted that any of the expansion mechanisms disclosed herein can be connected to the frame in a reversed orientation than shown in the drawings. For example, instead of connecting the rack 126 closer to the outflow end of the frame 102 and the pawl 124 closer to the inflow end of the frame 102, the expansion mechanism can be rotated 180 degrees with the rack 126 connected closer to the inflow end of the frame 102 and the pawl 124 connected closer to the outflow end of the frame 102. Further, the expansion cord for each expansion mechanism can be operatively connected to the pawl 124 of the expansion mechanism, instead of the rack, in order to move the pawl relative to the rack to radially expand the frame 102. Similarly, the release cord 174 for each expansion mechanism can be operatively connected to the rack 126 of the expansion mechanism, instead of the pawl, in order to disengage the teeth of the rack from the pawl.

Although less desirable, in alternative embodiments, the expansion mechanism 108 does not have a release cord 174 and the pawl 124 is not configured to move away from the rack.

Further, in alternative embodiments, the release cords 174 can be implemented in a prosthetic valve that does not have any expansion mechanisms 108. For example, the release cords 174 can be thread through or around selected struts 110 of the frame 102 and used to radially compress the frame via application of radial forces on the frame by the cords 174.

In still alternative embodiments, instead of expansion cords 158, the expansion mechanisms 108 can be actuated with other components of a delivery apparatus. For example, instead of expansion cords 158, the rack 126 can be releasably connected to an actuator member of a delivery apparatus in the form of a rod or shaft that is operable to apply a proximally directed force to the rack 126 and/or the pawl 124 can be releasably connected to another actuator member in the form of a rod or shaft that is operable to apply a distally directed force to the pawl 124 to radially expand the frame. If the expansion mechanism 108 is mounted to the frame in the reverse orientation, then an actuator member can apply a distally directed force to the rack and/or another actuator member can apply a proximally directed force to the pawl to radially expand the frame. Thus, it can be appreciated that an expansion mechanism 108 can be operated in either direction to radially expand or compress the frame by moving one or both of the rack and the pawl in a certain direction using any of various actuators of a delivery apparatus.

FIG. 17 is a schematic illustration of an expansion mechanism 200, according to another embodiment, that can be mounted to the frame 102 (along with one or more other expansion mechanisms 200), instead of expansion mechanisms 108, for radially expanding and compressing the frame 102 (and the prosthetic valve 100). The expansion mechanism 200 can be similar to the expansion mechanism 108 and can contain all of the same components including the housing 122, the rack 126, the expansion cord 158, and the knot 184. The other components of the expansion mechanism 108, such as the pawl 124 and the release cord 174, can also be included in the expansion mechanism 200 but are not shown in FIG. 13 for ease of illustration.

The operation of the expansion mechanism 200 is similar to the operation of the expansion mechanism 108 whereby the expansion cord 158 can cause the prosthetic valve 100 to foreshorten axially and expand radially by applying a proximally directed force on the loop section 158*a* of the cord 158. However, the expansion mechanism 200 can include first and second pulleys 202 and 204, respectively, which can reduce the amount of force needed to expand the prosthetic valve 100 as described below by reducing sliding friction of the cord.

The first pulley 202 can be mounted along an upper portion of the housing 122, such as on or adjacent the cord receiving member 148. The second pulley 204 can be mounted on the rack 126, such as on a lower portion of the rack in lieu of cord routing member 160. The pulleys 202, 204 can be conventional pulleys that can rotate about respective axles 206, 208. The expansion cord 158 can be reeved around the pulleys 202, 204 as shown in FIG. 17 such that a pulling force applied to the loop section 158*a* in the proximal direction causes the rack 126 to move further into the housing (upward in FIG. 17), causing the frame 102 to radially expand. The pulleys 202, 204 rotate as the rack 126 is moved to reduce or eliminate sliding friction of the cord against surfaces of the expansion mechanism.

In alternative embodiments, additional pulleys can be added at one or more other locations to further reduce the sliding friction of the cord 158 against adjacent surfaces of the expansion mechanism and/or to further increase the mechanical advantage of the assembly (which further decreases the force needed to pull the cords and expand the frame).

FIG. 18 is a schematic illustration of an expansion mechanism 300, according to another embodiment, that can be mounted to the frame 102 (along with one or more other expansion mechanisms 300), instead of expansion mechanisms 108, for radially expanding and compressing the frame 102 (and the prosthetic valve 100). In the embodiment of FIG. 18, the expansion mechanism 300 can comprise a housing 302, a pawl 304, and a rack 306.

Figure 14:
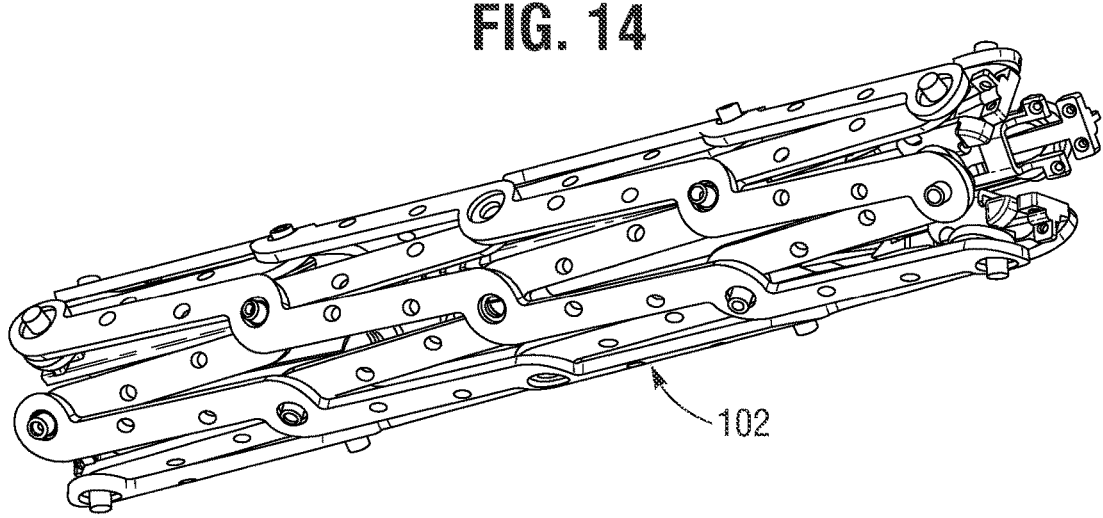
FIG. 14 is a perspective view of the prosthetic heart valve of FIG. 2 shown in a radially collapsed configuration.

The rack 306 can comprise a plurality of teeth 308. The pawl 304 can have corresponding teeth 305 (or a single tooth 305) that engage the teeth 308. The pawl 304 can move longitudinally within the housing 302 and can engage the teeth 308 of the rack 306 such that movement of the pawl is permissible in only one axial direction. The pawl 304 and the rack 306 can be coupled directly or indirectly to the frame 102 (not shown in FIG. 14) at axially spaced locations along the frame 102, such that axial movement of the pawl 304 in a certain direction (upward in the orientation of FIG. 18) relative to the rack 306 causes the frame 102 to expand radially.

An expansion cord 310 can be secured to the pawl 304 such that a pulling force applied to the expansion cord in the proximal direction (upward in FIG. 18) causes the pawl 304 to move relative to the rack to expand the frame. The engagement of the pawl 304 with the rack 306 prevents movement of the pawl 304 in the opposite direction (downward in FIG. 18) so as to prevent radial compression of the frame 102.

The expansion mechanism 300 can further comprise a biasing member that is configured to resiliently bias the pawl 304 in the expansion direction (i.e., the direction of movement of the pawl that produces radial expansion of the frame). The biasing member desirably applies a biasing force against the pawl that is sufficient to continuously expand the prosthetic valve over time if the native annulus in which the prosthetic is implanted dilates from disease or growth of the patient after the initial implantation.

In the illustrated embodiment, the biasing member comprises a spring 312 (e.g., a coil compression spring) positioned between the pawl 304 and an adjacent inner surface of the housing 302, as shown in FIG. 18. One end of the spring 312 can bear against an adjacent surface of the pawl 304 and the opposite end of the spring 312 can bear against the adjacent inner surface of the housing 302. The spring 312 can apply a constant biasing force against the pawl 304 in an axial direction (upward in the orientation of FIG. 18).

The biasing force is continuously applied by the spring 312 after the prosthetic valve 100 is implanted in a patient, thereby applying a constant expansion force to the prosthetic valve. In particular embodiments, the spring 312 (or other biasing member) is selected to have a biasing force that does not expand the prosthetic valve against the radial forces of the surrounding native annulus exerted against the prosthetic valve upon initial implantation at a desired deployment diameter but can further expand the prosthetic valve upon dilation of the native annulus caused by factors other than the expansion of the prosthetic valve. For example, the spring 312 (or other biasing member) can be selected to have a biasing force that is sufficient to radially expand the prosthetic valve in the absence of any outside forces acting against the prosthetic valve in a radial inward direction, but is not strong enough to overcome the forces exerted against the prosthetic valve by the native annulus in which the prosthetic valve is implanted. In particular embodiments, for example, the spring 312 (or other biasing member) provides a force of at least 3 N.

In some embodiments, the total expansion force provided by all expansion mechanisms 300 on the prosthetic valve can be at least 10 N, at least 50 N, at least 100 N, at least 150 N, or at least 200 N. The force provided by the spring 312 of each expansion mechanism is F/n, where F is the total expansion force and n is the total number of expansion mechanisms. Thus, where the prosthetic valve comprises three expansion mechanisms, each spring 312 can provide an expansion that is one third of the total expansion force, e.g., at least 3.33 N, at least 16.67 N, at least 33.33 N, at least 50 N, or at least 66.67 N. The total expansion force and the expansion force of each individual expansion mechanism having a spring can be the same for the embodiments of FIGS. 19-20, which are described below.

Thus, when the prosthetic valve 100 is initially implanted in a native annulus of a patient, the prosthetic valve can be expanded such that it fills the native annulus, such as by actuating one or more expansion mechanisms 300. The patient's anatomy may thus impart a compression force onto the prosthetic valve (i.e., a force that tends to cause the prosthetic valve to radially compress). The engagement of the pawl 304 with the rack 306 can prevent the frame 102 from compressing while the compression force acting on the prosthetic valve from the patient's anatomy can prevent further expansion of the prosthetic valve under the force of the spring 312. However, over time (day(s), week(s), month(s) or year(s)), the native annulus of the patient can relax and expand due to, for example, disease or growth of the patient, thereby reducing the compression force on the prosthetic valve. As this happens, the spring 312 forces the pawl 304 to move axially with respect to the rack 306, thereby expanding the frame 102. Thus, the prosthetic valve 100 can continually expand over time, even years after implantation in a patient, thereby reducing the need for additional surgical intervention to adjust or replace the prosthetic valve.

In some cases, due to the viscoelastic nature of the native heart valve, the native tissue can slightly expand immediately following implantation (for example, in the minutes, hours, or days following implantation). In this manner, the expansion force provided by the spring can fully expand the prosthetic valve to its final, intended diameter in the minutes, hours, or days immediately following implantation. In some applications, the physician can slightly under-expand the prosthetic valve using the one or more expansion mechanisms, such as to avoid rupturing or causing other trauma to the native tissue, and allow the expansion force of the spring to fully expand the prosthetic valve to its final diameter in the minutes, hours, or days immediately following implantation.

Another advantage of the biasing member is that as the prosthetic valve expands, such as due to tissue relaxation, the hemodynamics of the prosthetic valve can improve because effective outflow area of the prosthetic valve can increases and the pressure gradient across the prosthetic valve can decrease.

In alternative embodiments, various other types of biasing members can be used in lieu of or in addition to the compression spring 312. Without limitation, some examples of biasing members that can be used include various types of springs (e.g., tension springs, torsion springs, leaf springs), stretchable and/or elastic cords, and elastomeric bodies (e.g., a piece of silicone or polyurethane) that can be compressed upon application of force and resiliently expand back to its normal size and shape when the force is removed. Similarly, any of these types of biasing members can be used in lieu of or in addition the springs 408 and 514 in the embodiments described below.

Figure 19:
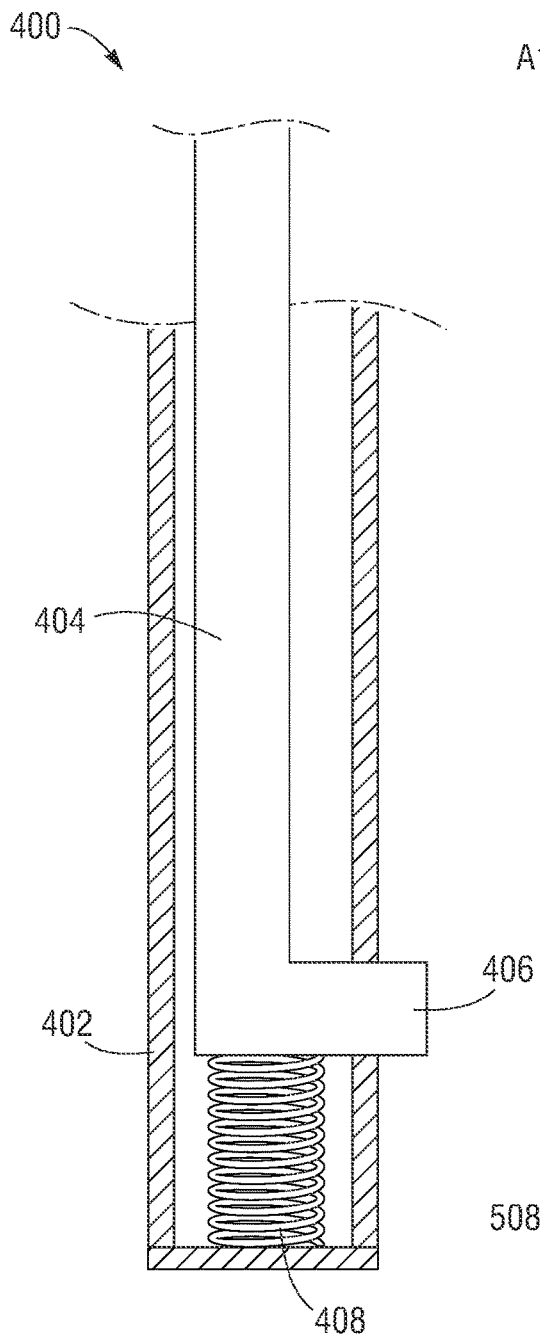
FIG. 19 shows a schematic diagram of another exemplary embodiment of an expansion mechanism that can be used with the prosthetic heart valve of FIG. 2.

FIG. 19 is a schematic illustration of an expansion mechanism 400, according to another embodiment, that can be mounted to the frame 102 (along with one or more other expansion mechanisms 400), instead of expansion mechanisms 108, for radially expanding and compressing the frame 102 (and the prosthetic valve 100). The expansion mechanism 400 can comprise a housing 402 and a rack 404 that can move axially within the housing. The rack 404 can have a post 406 at one end thereof that can be secured to the frame 102 of the prosthetic valve 100 (not shown in FIG. 19). The rack 404 can be configured to engage a pawl (not shown in FIG. 19), such as pawl 124, thereby allowing axial movement of the rack in one axial direction but not the opposite axial direction. Thus, axial movement of the rack 404 can cause the frame 102 to foreshorten axially and expand radially, as described in connection with the embodiment of FIGS. 1-12. An expansion cord (e.g., an expansion cord 158) can be operatively connected to the rack 404 as previously described in connection with the embodiment of FIGS. 1-12 to produce radial expansion of the frame 102 upon tensioning or increasing the force applied to the expansion cord.

The expansion mechanism 400 can further comprise a biasing member, such as the illustrated spring 408 (e.g., a coil compression spring), that applies a constant expansion force against the rack 404. As shown, the spring 408 can be positioned between the rack 404 and an adjacent inner surface of the housing 402 such that one end of the spring bears against the rack and other opposite end of the spring bears against the adjacent inner surface of the housing. The spring 408 can apply an axially directed biasing force against the rack 404. This can allow the expansion mechanism 400 to further expand the prosthetic valve 100 after implantation in a patient's native annulus as the native annulus expands over time, in a similar manner as discussed above in connection with the embodiment of FIG. 18. Thus, the spring 408 can be sized and configured as described above in connection with the embodiment of FIG. 18, except that the spring 408 applies a biasing force against the rack rather than the pawl. In alternative embodiments, any of the biasing members described above can be used in the expansion mechanism 400.

Figure 20:
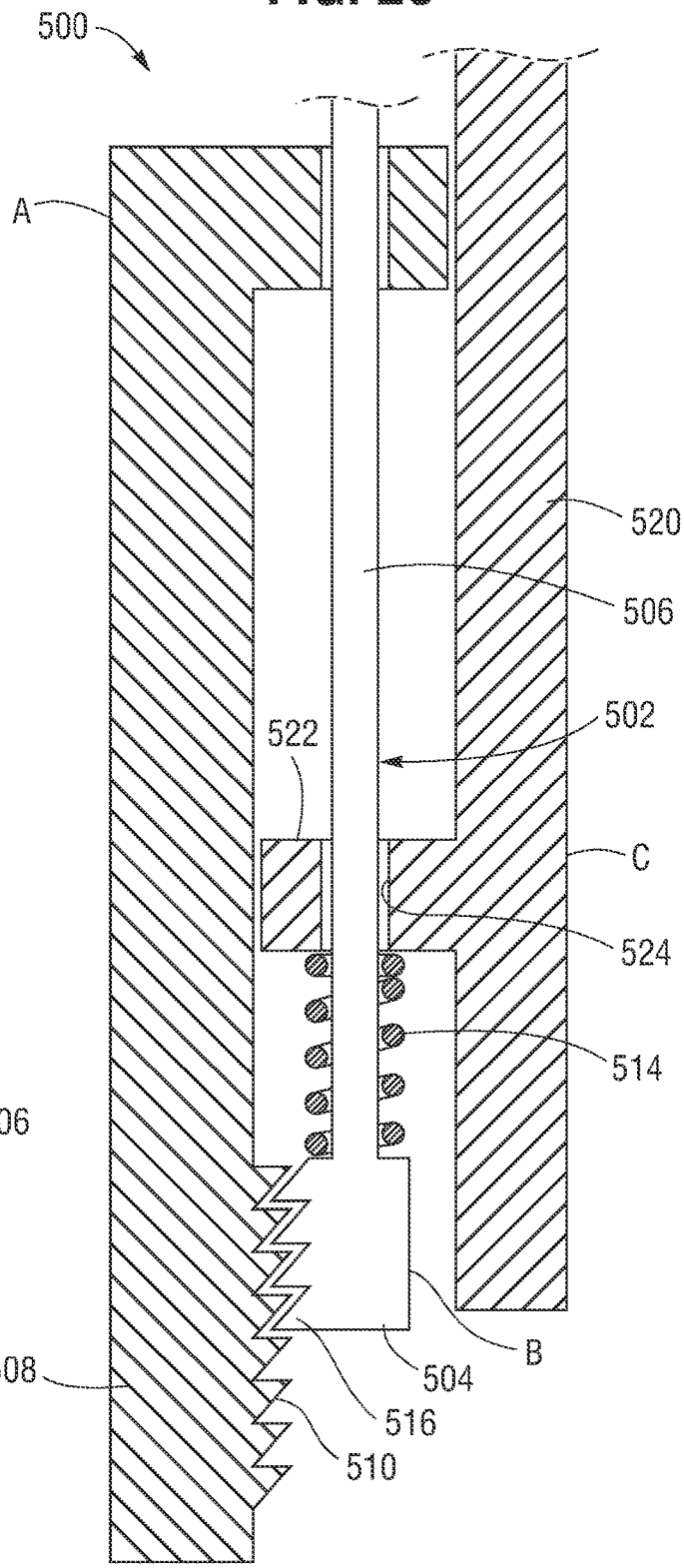
FIG. 20 shows a schematic diagram of another exemplary embodiment of an expansion mechanism that can be used with the prosthetic heart valve of FIG. 2.

FIG. 20 is a schematic illustration of an expansion mechanism 500, according to another embodiment, that can be mounted to the frame 102 (along with one or more other expansion mechanisms 500), instead of expansion mechanisms 108, for radially expanding and compressing the frame 102 (and the prosthetic valve 100). The expansion mechanism of FIG. 20 can comprise a pawl 502, a rack 508, and a housing 520. The pawl 502 can comprise an engagement portion 504 and an extension portion 506, wherein the engagement portion is positioned at an axial end of the extension portion. The rack 508 can have a plurality of ratchet teeth 510 that can engage one or more teeth 516 of the pawl 502 such that the pawl 502 and the rack 508 form a ratchet assembly. The housing 520 can have a laterally extending lip or projection 522 having a bore or lumen 524 extending therethrough. The extension portion 506 of the pawl 502 can extend through the bore 524 as shown. The pawl 502 and the housing 520 can be movable axially relative to each other in the proximal and distal directions as further explained below.

The teeth 516 of the pawl 504 can be configured to engage the teeth 510 of the rack 508 such that the pawl can move in one axial direction (upward in the orientation of FIG. 20) but cannot move in the opposite axial direction (downward in the orientation of FIG. 20). The pawl 502 and the rack 508 can be fixed relative to the frame 102 at axially spaced locations such that relative axial movement between the pawl and the rack produces radial expansion of the frame. The rack 508 and the pawl 502 can be directly or indirectly coupled to the frame 102 as previously described herein (e.g., these components can be coupled to respective hinges of the frame) so as to fix their axial locations relative to the frame.

For purposes of describing the operation of the expansion mechanism, the rack 508 is shown as being coupled to the frame 102 at location A and the pawl 502 is shown as being coupled to the frame 102 at location B. In particular embodiments, location A can be at or relatively closer to the outflow end 107 of the frame 102 than the inflow end 105 and location B can be at or relatively closer to the inflow end 105 of the frame 102 than the outflow end 107.

As such, applying an upwardly directed force to the pawl 502 (which can be in the proximal direction) causes the pawl 502 to move axially along the rack 508 while foreshortening the frame 102 in the axial direction and expanding the frame in the radial direction, as previously described herein. The engagement of the teeth 516 of the pawl 502 with the teeth 510 of the rack 508 resists movement of the pawl in the opposite direction to prevent radial compression of the frame 102. The expansion mechanism 500 can include an expansion cord (e.g., an expansion cord 158) operatively connected to the pawl 502 to produce radial expansion of the frame 102 upon tensioning or increasing the force applied to the expansion cord.

The expansion mechanism 500 can include a biasing member operatively connected to the ratchet assembly such that the potential energy of the biasing member increases upon the initial expansion of the prosthetic valve and the stored potential energy is used to further expand the prosthetic valve as the native annulus dilates or relaxes over time. As further shown in FIG. 20, for example, the biasing member comprises a compression spring 514 coaxially disposed around the extension portion 506 of the pawl 502 such that one end of the spring 514 can bear against an adjacent surface of the engagement portion 504 and the opposite end of the spring 514 can bear against an adjacent surface of the projection 522 of the housing 520. In this manner, the spring 514 (when loaded) exerts a biasing force against the projection 522 that causes the housing 520 to move axially (upward in FIG. 20) relative to the pawl 502 and the rack 508. In alternative embodiments, any of the biasing members described above can be used in the expansion mechanism 500.

The housing 520 can be directly or indirectly coupled to the frame 102 so as to fix the axial position of the housing relative to the frame 102 at a location spaced from the location where the pawl 502 is coupled to the frame and spaced from the location where the rack 508 is coupled to the frame 102. Typically, the housing 520 is coupled to the frame 102 at a location axially between the locations where the pawl 502 and the rack 508 are coupled to the frame. For purposes of describing the operation of the expansion mechanism, the housing 520 is shown as being coupled to the frame 102 at a location C, which is located axially between locations A and B.

During an implantation procedure for the prosthetic valve 100, the prosthetic valve can be radially expanded, such as by moving the pawl 502 proximally relative to the rack 508 (upward in FIG. 20). As the pawl 502 is moved axially relative to the rack 508, the engagement portion 504 of the pawl 502 moves toward the projection 522 of the housing and compresses the spring 514 (or further compresses the spring from an initially compressed state). In this manner, the initial expansion of the prosthetic valve is effective to establish or increase the potential energy of the spring 514. The compressed spring 514 exerts a biasing force against the housing 502 in a direction toward location A where the rack 508 is coupled to the frame (e.g., in the proximal direction, which is upward in FIG. 20). After the initial expansion of the prosthetic valve 100 in a native annulus of a patient, the patient's annulus resists further expansion under the force of the spring 514. The engagement of the teeth 516 of the pawl 502 and the teeth 510 of the rack 508 resists movement of the pawl 502 relative to the rack 508 under the biasing force of the spring 514 and the inward force exerted against the frame 102 by the native annulus to resist radial compression of the prosthetic valve. However, over time (e.g., in the minute(s), hour(s), day(s), week(s) or year(s) following implantation), as the native annulus relaxes and expands, the biasing force of the spring 514 can cause the housing 520 to move axially relative to the rack 508 (upward in FIG. 20), thereby further expanding the prosthetic valve without additional surgical intervention.

It should be noted that the expansion mechanism 500 can be actuated to initially expand the prosthetic valve by applying a force to the rack 508 in lieu of or in addition to applying a proximally directed force to the pawl 502. For example, a distally directed force (downward in FIG. 20) can be applied to the rack 508, such as by applying a pushing force against the rack with an actuator member of the delivery apparatus, in lieu or in addition to applying a proximally directed force to the pawl 502.

In other embodiments, in lieu or in addition to incorporating a biasing member in the expansion mechanisms (as in the embodiments of FIGS. 18-20), the frame of a prosthetic valve (e.g., frame 102) can be configured to be at least partially self-expandable such that it can further expand over time after the initial implantation. In one example, the struts of the frame 102 can be sized or shaped such that they store residual expansion forces that continue to expand the prosthetic valve over time in response to tissue relaxation or dilation after the initial implantation. In another example, the frame of a prosthetic valve (e.g., frame 102) can be self-expandable to a certain diameter but initially retained at a smaller diameter when initially implanted by the geometry of the leaflets and/or skirt and/or the connection between the frame and the leaflets and/or the connection between the frame or the skirt, which allow the frame to further expand over time in response to tissue relaxation or dilation after the initial implantation.

FIGS. 21 and 22A-22D show an exemplary embodiment of a distal end portion of a delivery apparatus 700 that can be used, for example, to implant a prosthetic valve (e.g., the prosthetic valve 100) in a native valve of a patient (e.g., a native aortic valve). Prior to implantation, the prosthetic valve can be crimped onto the delivery apparatus, which can include placing the radially compressed prosthetic valve within a delivery sheath of the delivery apparatus. If delivered transfemorally in a retrograde direction, a portion of the delivery apparatus and the prosthetic valve cross the patient's native aortic annulus and then the prosthetic valve is radially expanded within the native annulus, such as by actuating one or more expansion mechanism as described herein. However, during such an implantation procedure, it may become desirable to re-crimp the prosthetic valve in situ in order to reposition the prosthetic valve. This may require retracting the prosthetic valve and the delivery apparatus back into the descending aorta downstream of the native leaflets. While the one or more expansion mechanisms mounted on the frame of the prosthetic valve can compress the prosthetic valve, it may be difficult to radially compress the prosthetic valve enough to reinsert the prosthetic valve within the delivery sheath in situ. In some cases, contact between the distal end of the prosthetic valve and the native leaflets can inhibit re-crossing the native aortic valve. The delivery apparatus 700 facilitates re-crossing of the native aortic without such difficulties, as described below in detail.

The delivery apparatus 700 can comprise an inner shaft 702 extending co-axially through an outer shaft 704, and a nose cone 706 mounted on a distal end portion of the inner shaft 702. The proximal end portions of the inner shaft 702 and the outer shaft 704 can be connected to a handle (not shown), which can have various actuators for controlling relative movement between the shafts 702, 704, as previously described in connection with the delivery apparatus 600. The distal end portion 704d of the shaft 704 can be used as an outer sheath for housing the prosthetic valve during delivery through the patient's vasculature. The delivery apparatus 700 can have any of the features described above in connection with the delivery apparatus 600 but are not repeated here for sake of brevity.

As best shown in FIG. 21, the nose cone 706 in the illustrated embodiment comprises a tapered distal section 708, a cylindrical intermediate section 710, a tapered proximal section 712, and a flared skirt section 714 extending radially outwardly from the intermediate section 710. The nose cone 706 can include a lumen 716 extending the length of the nose cone through the distal section 708, the intermediate section 710, and the proximal section 710. The lumen 716 can be sized to allow the distal end portion of the shaft 702 to be inserted into the lumen and secured to the adjacent inner surface of the nose cone, such as with a suitable adhesive. The shaft 702 also can include a respective lumen sized to receive a guidewire 718 so that the delivery apparatus 700 can be advanced over the guidewire 718 through the vasculature of the patient, as known in the art.

The intermediate section 710 can have an outer diameter that is smaller than the proximal-most end of the distal section 708 so as to define an annular shoulder 720 between the intermediate section 710 and the distal section 708. The diameter of the intermediate section 710 desirably is sized to allow the sheath 704d to extend over the proximal section 712 and the intermediate section 710 and to allow the distal-most end of the sheath 704d to abut the annular shoulder 720. The maximum diameter of the distal section 708 (at the shoulder 720) desirably is the same or substantially the same as the outer diameter of the sheath 704d to provide a smooth, atraumatic transition between the nose cone and the sheath.

The proximal section 712 can taper from a larger diameter at the proximal-most end of the intermediate section 710 to a smaller diameter at the proximal-most end of the nose cone. This aids is retracting the nose cone 706 back through the prosthetic valve and into the sheath after the prosthetic valve has been expanded. However, in other embodiments, the proximal section 712 can other shapes or configurations, such as a cylindrical shape similar to the intermediate section 710.

The skirt section 714 is biased to a radially expanded state as shown in FIG. 21 in the absence of outside forces on the skirt section but is movable or foldable between a first compressed or folded position extending proximally over the proximal section 712 (see FIG. 22A) and a second compressed or folded position extending distally over the intermediate section 710 (see FIG. 22D). When it is in the radially expanded state, the skirt section 714 has a maximum diameter D that is greater than the adjacent end of the prosthetic valve 100 (the inflow end of the prosthetic valve in the illustrated embodiment) to shield the adjacent end of the prosthetic valve from native tissue during re-crossing of the native valve (see FIG. 22C). Additionally, the skirt section 714 desirably has a conical shape that flares in a direction from its connection to the intermediate section 710 toward the proximal section 712.

The nose cone 702 can made of a low durometer polymer, such as Pebax (e.g., a 35-shore Pebax). The skirt section 714 can be integrally formed with the remaining sections of the nose cone. For example, the entire nose cone can have one-piece unitary construction formed by molding, for example. The skirt section 714 can exhibit sufficient flexibility such that it can be bent to the first folded position and to the second folded position.

In the illustrated embodiment, the skirt section 714 has a closed annular shape along its entire length, meaning that it extends continuously around its central axis through 360 degrees along its entire length. In alternative embodiments, the skirt section 714 can have other shapes or configurations. For example, the skirt section 717 can include one or more longitudinally extending gaps extending partially or fully along the length of the skirt section so as to separate skirt section into multiple flaps or sections that can bend or deflect relative to each other.

During an implantation procedure, the prosthetic valve 100 is coupled to the delivery apparatus 700 and crimped to a collapsed configuration as shown in FIG. 22A. The prosthetic valve can be releasably connected to a positioning member (similar to positioning member 608) of delivery apparatus 700 using cords 158, 174, as described above. The skirt section 714 can be folded in a proximal direction to the first folded position and the sheath 704d can be placed over the prosthetic valve 100, as well as the skirt section 714 and the intermediate section 710 of the nose cone, as shown in FIG. 22A. As shown in FIG. 22A, the crimped prosthetic valve can be positioned proximal to the nose cone 706 within the sheath 104d. In other embodiments, the crimped prosthetic valve can be placed at least partially around the skirt section 714 (after placing it in the first folded position) and optionally around the intermediate section 710 of the nose cone.

The delivery apparatus 700 and the prosthetic valve 700 can then be inserted into the patient's vasculature and advanced through the vasculature using a transfemoral, retrograde delivery approach. The prosthetic valve 100 is advanced through the aortic arch, the ascending aorta and partially across the native aortic valve to position at least a portion of the prosthetic valve within the native valve.

In order to deploy the prosthetic valve from the delivery apparatus, the nose cone 706 can be advanced distally (e.g., by advancing the inner shaft 702) and/or retracting the sheath 704d. This allows the skirt section 714 to self-expand under its own resiliency to the expanded state as shown in FIG. 22B. The prosthetic valve 100 can then be expanded using the techniques described above (e.g., actuating one or more expansion mechanisms 108).

If the prosthetic valve 100 needs to be retracted back into the ascending aorta for repositioning, the prosthetic valve can be radially compressed using the techniques described above (e.g., actuating one or more expansion mechanisms 108 in reverse). After radially compressing the prosthetic valve, the sheath 704d can be advanced over the proximal end portion of the prosthetic valve and the skirt section 714 can be retracted against the distal end portion of the prosthetic valve, as depicted in FIG. 22C. The skirt section 714 desirably is sized to extend at least partially over the distal end portion of the prosthetic valve in this position. The delivery apparatus 700 and the prosthetic valve 100 can then be retracted back into the aortic root or the ascending aorta. If the physician inadvertently retracts the delivery apparatus and the prosthetic valve prior to placing the sheath 704d and the skirt section 714 against the ends of the prosthetic valve, the skirt section 714 can flex upon contact with the native leaflets to avoid or minimize trauma of the native leaflets. Thereafter, the skirt section 714 and the sheath 704d can be placed against the opposing end portions of the prosthetic valve as shown in FIG. 22C.

While in the configuration shown in FIG. 22C, the delivery apparatus 700 and the prosthetic valve 100 can be advanced back through the native aortic valve. Advantageously, the conical shape of the distal section 708 and the skirt section 714 of the nose cone 706 forms a smooth transition from the guide wire 718 to the valve 100 to facilitate re-crossing. Furthermore, as noted above, the skirt section 714 shields the distal end portion of the prosthetic valve so that the metal components of the frame 102 (in particular, the apices at the distal end of the frame) can slide past the native leaflets without catching or causing trauma to the native leaflets.

Once the prosthetic valve 100 is positioned at the desired location, the sheath 704d can be retracted, the nose cone 706 can be advanced distally, and then the prosthetic valve can be expanded and released from the delivery apparatus 700 as described above. After the prosthetic valve 100 is released from the delivery apparatus, the sheath 704d can be advanced distally over the skirt section 714 and/or the nose cone can be retracted proximally into the sheath, which causes the skirt section 714 to bend or fold to the second folded position, as depicted in FIG. 22D. In FIG. 22D, the sheath 704d extends partially over the skirt section 714. If desired, the sheath 704d can be advanced over the entire extent of the skirt section 714 and the distal-most end of the sheath can be placed in contact with the shoulder 720. Advancing the sheath 704d over the entire extent of the skirt section 714 causes the skirt section 714 to fully collapse against the intermediate section 710. After partially or fully covering the skirt section 714, the delivery apparatus 700 can be withdrawn from the patient's body.

In alternative embodiments, the nose cone 706 can be implemented or incorporated in other delivery apparatus, which can be used to deliver a prosthetic valve 100 or other types of prosthetic valves, including any types of mechanically expandable valves or non-mechanically expandable valves (e.g., self-expandable valves and balloon-expandable valves). For example, the nose cone 706 can be implemented or incorporated in any of the delivery apparatuses disclosed in U.S. Publication No. 2018/0153689, which is incorporated herein by reference. U.S. Publication No. 2018/0153689 discloses mechanically expandable heart valves and delivery apparatuses therefor. In another example, the nose cone can be implemented in any of the delivery apparatuses disclosed in U.S. Publication No. 2014/0343670, which is incorporated herein by reference. U.S. Publication No. 2014/0343670 discloses self-expandable prosthetic heart valves and delivery apparatuses therefor. In another example, the nose cone can be implemented in any of the delivery apparatuses disclosed in U.S. Publication No. 2017/0065415, which is incorporated herein by reference. U.S. Publication No. 2017/0065415 discloses balloon-expandable prosthetic heart valves and delivery apparatuses therefor.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.). The disclosed embodiments can also be used to implant prostheses in other lumens of the body. Further, in addition to prosthetic valves, the delivery assembly embodiments described herein can be adapted to deliver and implant various other prosthetic devices such as stents and/or other prosthetic repair devices.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

We claim:

1. A radially expandable prosthetic valve, comprising:
   an annular frame comprising an inflow end and an outflow end and being radially collapsible and expandable between a radially collapsed configuration and a radially expanded configuration;
   at least one expansion mechanism comprising a first member attached to the frame at a first location and a second member attached to the frame at a second location axially spaced from the first location;
   a cord that extends through a first opening in the second member, extends at least partially along the second member in a first direction, is reeved around a cord routing member of the second member, extends at least partially along the second member in a second direction opposite the first direction, and extends through a second opening in the second member; and
   wherein the cord routing member is spaced apart in an axial direction from both the first opening and the second opening, and
   wherein applying a proximally directed force to a first portion of the cord causes the cord to move relative to the second member and the second member to move relative to the first member, which causes the frame to foreshorten axially and expand radially.

2. The prosthetic valve of claim 1,
   wherein applying a proximally directed force to a second portion of the cord releases the cord from the expansion mechanism.

3. The prosthetic valve of claim 1, further comprising a stop member coupled to the cord and sized to prevent the cord from being pulled through the expansion mechanism when the proximally directed force is applied to the first portion of the cord.

4. The prosthetic valve of claim 3, wherein the stop member comprises a knot.

5. The prosthetic valve of claim 1, wherein the expansion mechanism further comprises a housing and the second member is slidable at least partially within the housing.

6. The prosthetic valve of claim 5, wherein the cord extends through a first portion of the housing, around the portion of the second member and through a second portion of the housing, in that order.

7. The prosthetic valve of claim 6, wherein applying the proximally directed force to the first portion of the cord pulls the second member through the housing towards the first location on the frame.

8. The prosthetic valve of claim 1, further comprising a locking mechanism configured to retain the frame in the radially expanded configuration.

9. The prosthetic valve of claim 1, wherein the at least one expansion mechanism comprises a ratchet assembly.

10. The prosthetic valve of claim 9, wherein the first member comprises one of a rack and a pawl of the ratchet assembly and the second member comprises the other of the rack and the pawl of the ratchet assembly.

11. The prosthetic valve of claim 10, wherein the rack comprises an elongated bar comprising a plurality of ratchet teeth arrayed along a length of the bar;
    wherein the rack is movable with respect to the pawl;
    wherein applying the proximally directed force to the first portion of the cord causes the rack to move in the second direction thereby causing the annular frame to foreshorten axially and expand radially; and
    wherein engagement of the pawl with one of the ratchet teeth prevents movement of the rack in the first direction to prevent radial compression of the annular frame.

12. The prosthetic valve of claim 11, wherein the pawl comprises an engagement portion that is configured to engage the ratchet teeth of the rack, a release portion extending away from the rack, and an intermediate portion between the engagement portion and the release portion, wherein an inwardly directed radial force applied to the release portion causes the engagement portion to disengage from the ratchet teeth to allow movement of the pawl along the rack in the first direction.

13. The prosthetic valve of claim 12, wherein the cord is a first cord and the prosthetic valve further comprises a second cord connected to the release portion of the pawl such that a pulling force applied to the second cord causes the engagement portion to disengage from the ratchet teeth.

14. The prosthetic valve of claim 13, wherein the second cord comprises a loop that extends through first and second openings in the release portion of the pawl.

15. The prosthetic valve of claim 13, wherein the at least one expansion mechanism comprises at least two expansion mechanisms and the second cord of each expansion mechanism is configured such that a pulling force applied to the second cord of each expansion mechanism causes the frame to compress radially.

16. The prosthetic valve of claim 1, wherein the frame comprises a plurality of struts connected to each other at a plurality of pivot joints and the second member comprises a post that extends into openings in two of the struts to form one of the pivot joints.

17. The prosthetic valve of claim 10, wherein the expansion mechanism further comprises a retaining member configured to apply a biasing force to the pawl so as to resiliently retain the pawl in engagement with the rack.

18. The prosthetic valve of claim 1, wherein the cord is reeved is a pulley of the cord routing member.

19. The prosthetic valve of claim 1, wherein the cord is a suture.

20. The prosthetic valve of claim 13, wherein the second cord is a suture.

21. The prosthetic valve of claim 1, in combination with a delivery apparatus comprising a handle, wherein the first portion of the cord is operatively connected to the handle.

22. The prosthetic valve of claim 1, wherein the expansion mechanism further comprises a biasing member configured to exert a biasing force against the second member in the second direction, wherein the biasing force is selected such that when the prosthetic valve is implanted within a native heart valve annulus, the second member is caused to move in the second direction under the biasing force and further expand the frame as the native annulus enlarges over time.

23. The prosthetic valve of claim 22, wherein the biasing member comprises a spring.

24. A radially expandable prosthetic valve, comprising:
an annular frame comprising an inflow end and an outflow end and being radially collapsible and expandable between a radially collapsed configuration and a radially expanded configuration;
at least one expansion mechanism comprising a first member attached to the frame at a first location and a second member attached to the frame at a second location axially spaced from the first location;
a cord operatively connected to the first and second members,
wherein the cord extends through a first opening in the second member, extends at least partially along the second member in a first direction, is reeved around a cord routing member of the second member, extends at least partially along the second member in a second direction opposite the first direction, and extends through a second opening in the second member, such that applying a force to the cord causes the second member to move relative to the first member with a mechanical advantage greater than 1,
wherein movement of the second member relative to the first member causes the frame to radially expand, and
wherein the cord routing member is spaced apart in an axial direction from both the first opening and the second opening; and
a knot coupled to the cord and sized to prevent the cord from being pulled through the expansion mechanism when a proximally directed force is applied to the cord.

25. The prosthetic valve of claim 24, wherein the mechanical advantage is at least 2:1.

26. The prosthetic valve of claim 24, wherein the cord extends distally at least partially along the expansion mechanism, around a portion of the second member, and proximally at least partially along the expansion mechanism.

* * * * *